(12) United States Patent
Dekel et al.

(10) Patent No.: US 8,632,803 B2
(45) Date of Patent: Jan. 21, 2014

(54) SYSTEM FOR DELIVERY OF PROTEIN IN INSOLUBLE FIBRILLAR OR AGGREGATE FORM

(75) Inventors: Yaron Dekel, Petach-Tikva (IL); Rimona Margalit, Givataim (IL)

(73) Assignee: Ramot At Tel-Aviv University Ltd., Tel Aviv (IL)

( * ) Notice: Subject to any disclaimer, the term of this patent is extended or adjusted under 35 U.S.C. 154(b) by 309 days.

(21) Appl. No.: 12/920,096

(22) PCT Filed: Feb. 18, 2009

(86) PCT No.: PCT/US2009/034388
§ 371 (c)(1), (2), (4) Date: Aug. 27, 2010

(87) PCT Pub. No.: WO2009/108554
PCT Pub. Date: Sep. 3, 2009

(65) Prior Publication Data
US 2011/0008422 A1  Jan. 13, 2011

Related U.S. Application Data

(60) Provisional application No. 61/031,985, filed on Feb. 27, 2008.

(51) Int. Cl.
*A61K 9/127* (2006.01)
*A61K 9/14* (2006.01)
*A61K 38/28* (2006.01)
*A61P 3/10* (2006.01)

(52) U.S. Cl.
USPC .............................. 424/450; 424/491; 514/5.9

(58) Field of Classification Search
None
See application file for complete search history.

(56) References Cited

U.S. PATENT DOCUMENTS

| 6,852,694 B2 * | 2/2005 | Van Antwerp et al. ........ 514/6.3 |
| 2004/0096852 A1 * | 5/2004 | Dobson et al. .................... 435/6 |

FOREIGN PATENT DOCUMENTS

| WO | 02/42321 A2 | 5/2002 |
| WO | 03/015755 A1 | 2/2003 |
| WO | WO 03/015755 * | 2/2003 ............... A61K 9/14 |
| WO | 2007/067597 A2 | 6/2007 |

OTHER PUBLICATIONS

Jimenez et al., PNAS 99: 9196-9201, 2002.*
International Search Report in PCT/US2009/034388.
Written Opinion (Form PCT/ISA/237) in PCT/US2009/034388.
Yerushlmi, et al. "Molecular and Cellular Studies of Hyaluronic Acid-Modified Liposomes as Bioadhesive Carriers for Topical Drug Delivery in Wound Healing," Achieves of Biochemistry and Biophysicis, vol. 313, No. 2, pp. 267-273 (Sep. 1, 1994).
Sarmento, et al. "Probing insulin's secondary structure after entrapment into alginate/chitosan nanoparticles," European Journal of Pharmaceutics and Biopharmaceutics, vol. 65, No. 1, pp. 10-17 (Dec. 1, 2006).
Whittingham, et al. "Insulin at pH 2: Structural Analysis of the Conditions Promoting Insulin Fibre Formation," Journal of Molecular Biology, vol. 318, pp. 479-490 (2002).

* cited by examiner

*Primary Examiner* — Robert A Wax
*Assistant Examiner* — Danah Al-Awadi
(74) *Attorney, Agent, or Firm* — Browdy and Neimark, PLLC

(57) ABSTRACT

A pharmaceutical composition containing a therapeutic protein which is particularly amenable to oral administration by providing stability in the gastrointestinal tract. Insoluble fibrils or aggregates of the therapeutic protein in the pharmaceutical composition are encapsulated in a lipidated glycosaminoglycan particle, coated with a multi-layer of lipids and lipid-glycosaminoglycan conjugates, or present as unencapsulated and uncoated insoluble fibrils or aggregates.

33 Claims, 11 Drawing Sheets

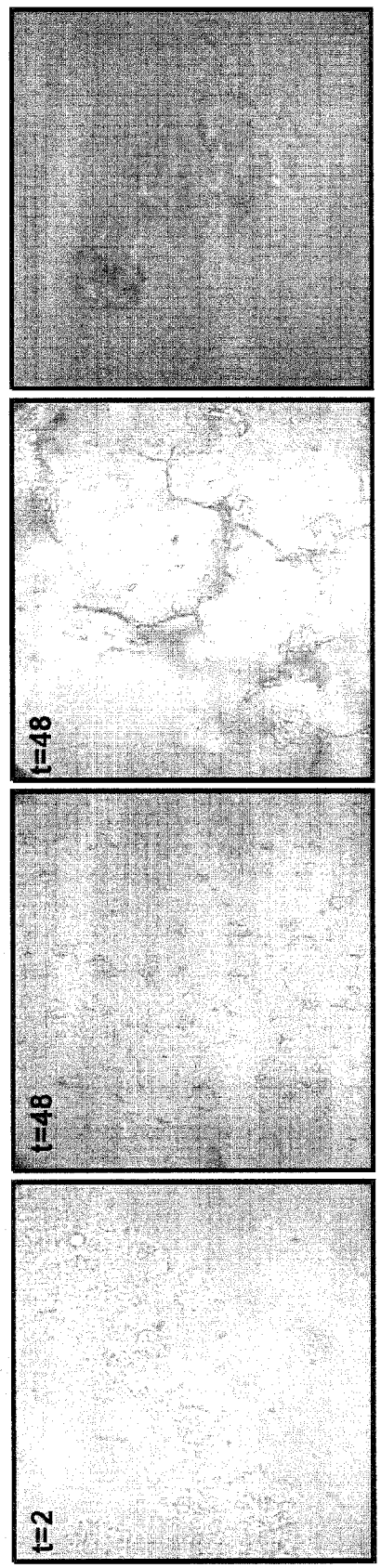
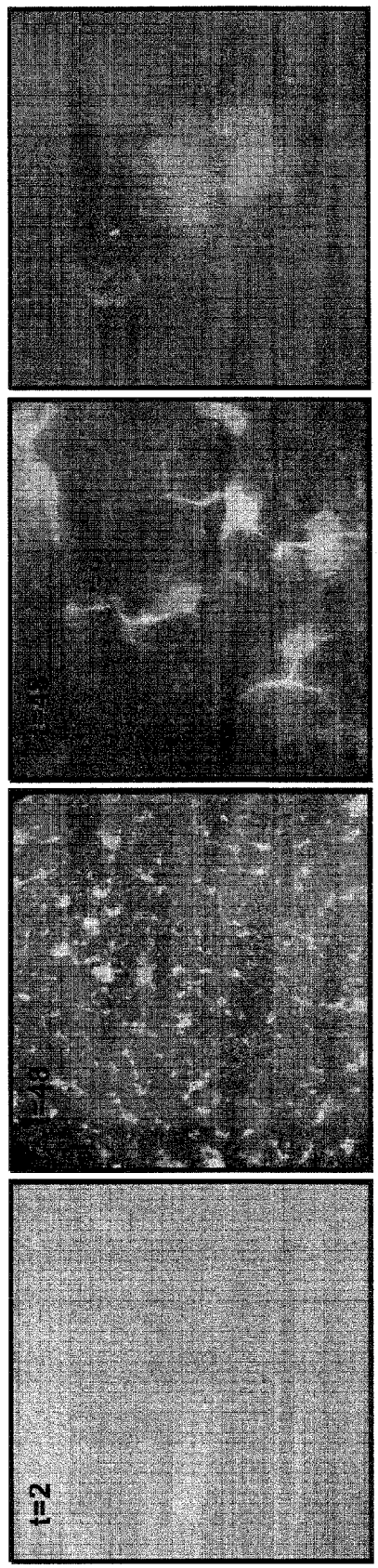
Fig. 4A  Fig. 4C  Fig. 4E  Fig. 4G
Fig. 4B  Fig. 4D  Fig. 4F  Fig. 4H

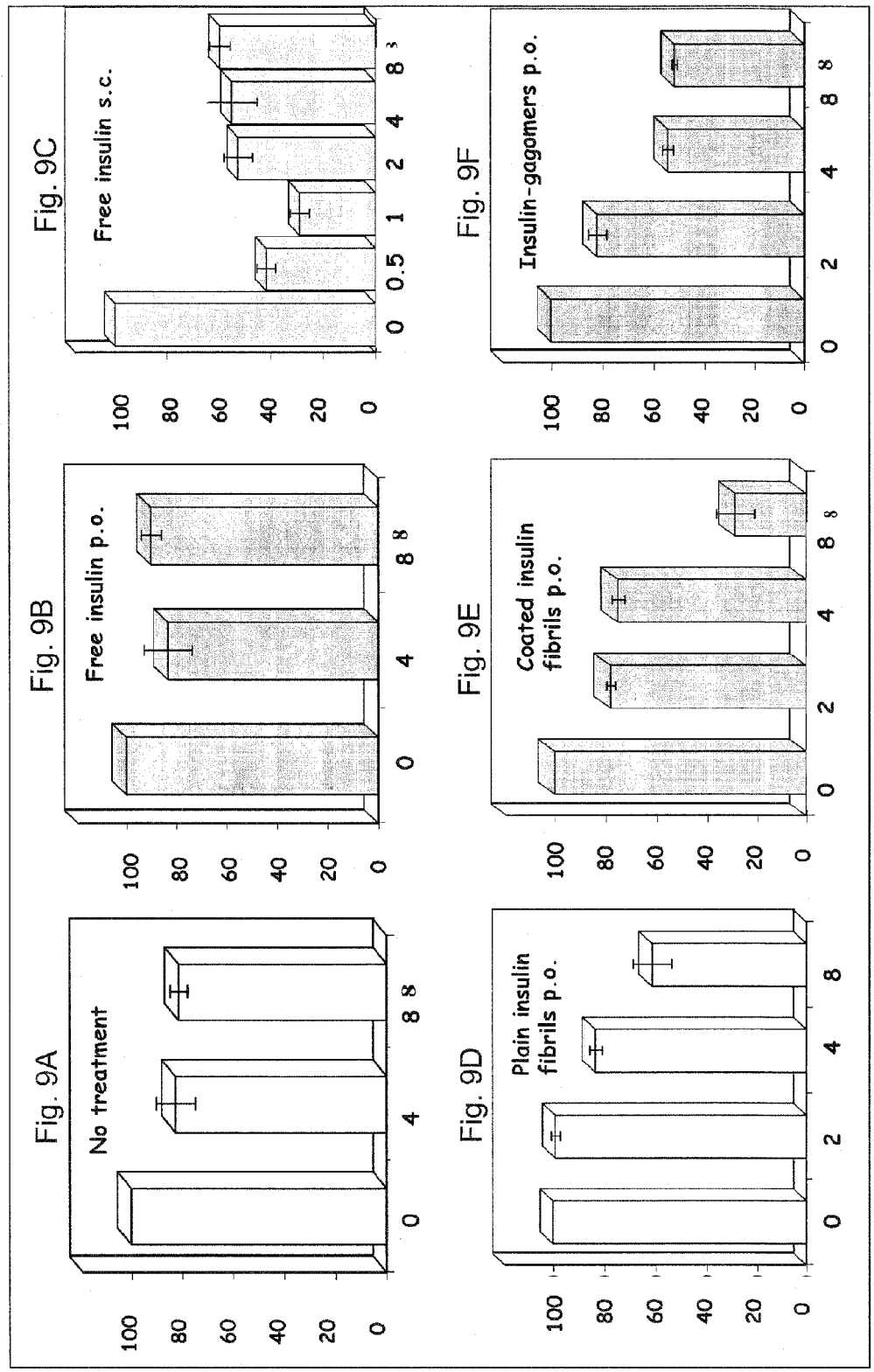

Fig. 10A — 2 hours
Fig. 10B — 24 hours
Fig. 10C — 48 hours
Fig. 10D — 96 hours
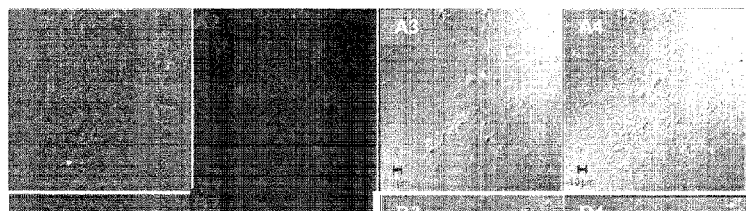
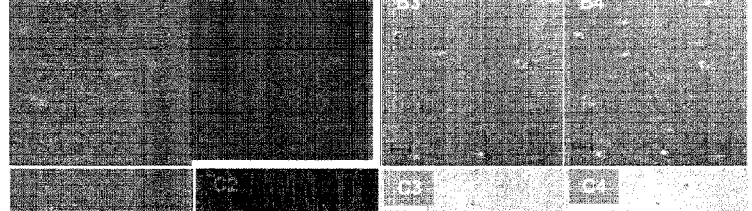
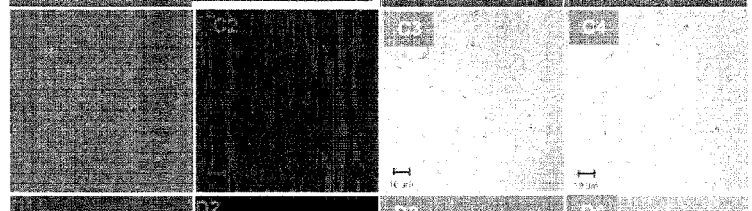
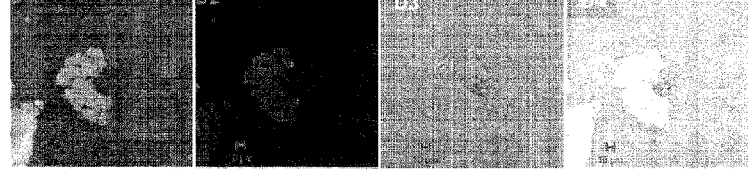
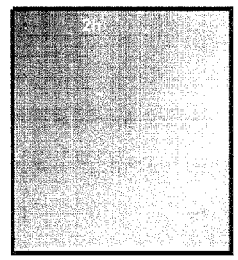
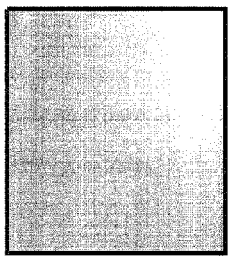
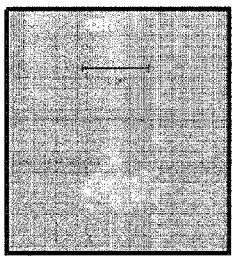
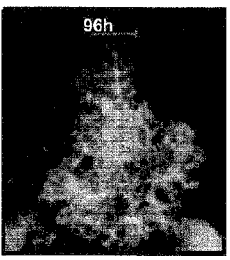
Fig. 11A    Fig. 11B    Fig. 11C    Fig. 11D

SYSTEM FOR DELIVERY OF PROTEIN IN INSOLUBLE FIBRILLAR OR AGGREGATE FORM

BACKGROUND OF THE INVENTION

1. Field of the Invention

The present invention relates to a protein delivery system.

2. Description of the Related Art

Proper glycaemic control is crucial for diabetic patients to slow down disease progression and its long-term chronic complications. The need for life-long daily (or more) insulin injections (the standard treatment for type I and eventually for type II diabetics) decreases patient compliance, can be painful and runs the risk of local infections (Gonzalez et al., 2006; and Lassmann-Vague et al., 2006). Currently, the oral route is not feasible for insulin which, like most peptides and proteins, is prone to fast clearance and enzyme-catalyzed degradation by the harsh environments along the gastro-intestinal tract (GIT), resulting in <0.5% insulin bioavailability (Cefalu et al., 2004).

Insulin—native or chemically modified—formulated in a carrier that will withstand the harsh GIT conditions, has been tested. To gain the most from each administered dose, such a carrier should, furthermore, act through muco-adhesion as a slow-release insulin-depot within the GIT. Carrier types tested for the task include hydrogels, microspheres, nanoparticles, microemulsions and liposomes (Morishita et al., 2006).

Glycosaminoglycans, or mucopolysaccharides, along with collagen, are the chief structural elements of all connective tissues. Glycosaminoglycans, or gags, are large complexes of polysaccharide chains associated with a small amount of protein. These compounds have the ability to bind large amounts of water, thereby producing a gel-like matrix that forms the body's connective tissues. Gags are long chains composed of repeating disaccharide units (aminosugar-acidic sugar repeating units). The aminosugar is typically glucosamine or galactosamine. The aminosugar can also be sulfated. The acidic sugar may be D-glucuronic acid or L-iduronic acid. In vivo, gags other than hyaluronic acid are covalently bound to a protein, forming proteoglycan monomers. The polysaccharide chains are elongated by the sequential addition of acidic sugars and aminosugars.

Among the most common gags are hyaluronic acid, keratan sulfate, chondroitin sulfate, heparin sulfate, and dermatin sulfate. Gags may be chemically modified to contain more sulfur groups than in their initially extracted form. In addition, gags may be partially or completely synthesized and may be of either plant or animal origin.

Hyaluronic acid is a naturally occurring member of the glycosaminoglycan family which is present in particularly high concentration in the cartilage and synovial fluid of articular joints, as well as in vitreous humor, in blood vessel walls, and umbilical cord and other connective tissues. Hyaluronic acid can be in a free form, such as in synovial fluid, and in an attached form, such as an extracellular matrix component. This polysaccharide consists of alternating N-acetyl-D-glucosamine and D-glucuronic acid residues joined by alternating β-1,3-glucuronidic and β-1,4-glucosaminidic bonds. In water, hyaluronic acid dissolves to form a highly viscous fluid. The molecular weight of hyaluronic acid isolated from natural sources generally falls within the range of $5 \times 10^4$ up to $10^7$ daltons. Hyaluronic acid has a high affinity for the extracellular matrix and to a variety of tumors, including those of the breast, brain, lung, skin, and other organs and tissues.

There are two basic classes of drug carriers: particulate systems, such as cells, microspheres, viral envelopes, and liposomes; and non-particulate systems, which are usually soluble systems, consisting of macromolecules such as proteins or synthetic polymers.

U.S. Pat. No. 5,733,892 to Sakurai et al. discloses lipidated glycosaminoglycan molecules which are soluble in aqueous solution (i.e., not insoluble particles). WO 03/015755 discloses a similar system but of lipidated glycosaminoglycan particles which form suspensions of insoluble particles in an aqueous phase. WO 2006/050246 discloses an improvement of the lipidated glycosaminoglycan particles of WO 03/015755 to provide a satisfactory solution to the problems associated with targeted delivery of water insoluble and poorly water soluble drugs such as paclitaxel (taxol).

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

SUMMARY OF THE INVENTION

The present invention provides a pharmaceutical composition in which insoluble fibrils or aggregates of a therapeutic protein, which protein is active in a soluble monomeric form, are either encapsulated in a lipidated glycosaminoglycan particle, coated with a multi-layer of lipids and lipid-glycosaminoglycan conjugates, or present as unencapsulated and uncoated insoluble fibrils or aggregates. This pharmaceutical composition is particularly amenable to oral administration, providing stability to the protein in the gastro-intestinal tract.

The present invention also provides a method for preparing the active ingredient of the pharmaceutical composition as well as a method for treating diabetes by administering insulin as the therapeutic protein in insoluble fibrillar or aggregate form.

Another aspect of the present invention relates to an improved method for treating an indication with a therapeutic protein effective for the indication, where the improvement lies in administering encapsulated, coated, or unencapsulated and uncoated insoluble fibrils or aggregates of the therapeutic protein instead of its soluble active form.

BRIEF DESCRIPTION OF THE DRAWINGS

FIGS. 1A-1H are light and fluorescence microscopy images of bovine and of human recombinant insulin fibrils. Magnification was ×100. FIG. 1A shows light microscopy of a dried sample originating from 5 mg/ml acidic bovine insulin after 24 hours of incubation with agitation. The rectangle marks one insulin spherolite. FIG. 1B is a sample similar to FIG. 1A, stained with Th-S and viewed under a fluorescent microscope Excitation and emission were at 450 nm and 480 nm, respectively. FIG. 1C is a sample similar to FIG. 1A, but with a low dose of human recombinant insulin fibrils, in water alone. FIG. 1D is a sample similar to FIG. 1C, but with the addition of PBS to a final concentration of 10 mM. FIG. 1E shows light microscopy of a sample originating from 5 mg/ml acidic human recombinant insulin (containing a trace of FITC-Insulin) after 2 weeks of incubation with no agitation. FIG. 1F shows fluorescence microscopy of the sample shown in FIG. 1E, excitation and emission were at 480 nm and at 530 nm.

FIGS. 2A-2E show the effects of incubation time on formation of the coated insulin fibrils. Upper panels (FIGS. 2A, 2C, 2E and 2G) are light micrographs, lower panels (FIGS. 2B, 2D, 2F and 2H) are fluorescent micrographs. FIGS. 2A-2B: 2 hours of incubation. FIGS. 2C-2D: 24 hours of incubation. FIGS. 2E-2F: 192 hours of incubation. FIGS. 2G-2H: Stability in GIF. Fluorescence microscographs of coated insulin fibrils (separated from excess free insulin). FIG. 2G: time=0, FIG. 2H: after two hours of incubation in GIF.

FIG. 3A—the Namarsky image; FIG. 3B—the fluorescent image; FIG. 3C—a composite of FIG. 3A-3B.

FIGS. 4A-4H are light and fluorescence microscopy images of the effects of incubation time on formation of insulin-gagomer particles (bovine insulin containing trace FITC-insulin). Upper panels (FIGS. 4A, 4C, 4E and 4G) are light micrographs, lower panels (FIGS. 4B, 4D, 4F and 4H) are fluorescent micrographs. FIGS. 4A-4B: 2 hours of incubation (magnification ×100). FIGS. 4C-4D: 48 hours of incubation (magnification ×40). FIGS. 4E-4F: same as FIGS. 4C-4D, but higher magnification (×100). FIGS. 4G-4H: Stability in GIF. Fluorescent micrographs of insulin-gagomer particles (separated from excess free insulin). FIG. 4G: time=0 FIG. 4H: after two hours of incubation in GIF.

FIG. 5A—the Namarsky image; FIG. 5B—the fluorescent image; FIG. 5C—a composite of FIGS. 5A and 5B.

FIG. 6A: an insulin-gagomer particle at the higher-end of the particle size range. FIG. 6B: insulin-gagomer particles at the lower-end of the particle size range. FIG. 6C: similar to FIG. 6A, except "empty" gagomers.

FIGS. 9A-9F show the blood glucose levels (BGL) of diabetic mice as a function of time and treatment. Each bar is an average of 4-9 mice and the error bars are the SEM. A single dose of insulin, at the selected formulation (detailed below) was given at time=0. The animals had no access to food from time=0. At time=4 hours, immediately after withdrawing blood samples, the animals had access to food for 20 minutes, and thereafter no access to food until the end of the experiment (at time=8 hours). Treatment doses were 1.5 IU/kg body for the s.c injection, and 10 IU per mouse for the p.o gavage administration. FIG. 9A—Untreated mice. FIG. 9B—Mice treated p.o by free (i.e., non-fibrillated) insulin. FIG. 9C—Mice treated s.c by free insulin. FIG. 9D—Mice treated p.o by plain insulin fibrils. FIG. 9E—Mice treated p.o by coated insulin fibrils. FIG. 9F—mice treated p.o by gagomeric insulin.

FIGS. 10A-10D show confocal microscopy images of double labeled coated insulin fibrils formation after 2 (FIG. 10A), 24 (FIG. 10B), 48 (FIG. 10C) and 96 (FIG. 10D) hours of incubation. Magnification ×40. Excitation and emission were at 480 nm and at 530 nm, respectively for FITC-insulin and at 543 nm and at 560 nm for DPPE-Rhodamine. The scale bar (bottom left) is 10 µm. Panels 1—the FITC image; 2—the Rhodamine image; 3—a Namarsky image; 4—A composite of 1-3.

FIGS. 11A-11D show confocal microscopy images of insulin fibrils formation after 2 (FIG. 11A), 24 (FIG. 11B), 48 (FIG. 11C) and 96 (FIG. 11D) hours of incubation. Magnification ×40. Excitation and emission were at 480 nm and at 530 nm, respectively for FITC-insulin and at 543 nm. The scale bar is 10 µm.

DETAILED DESCRIPTION OF THE INVENTION

Figure 1A:
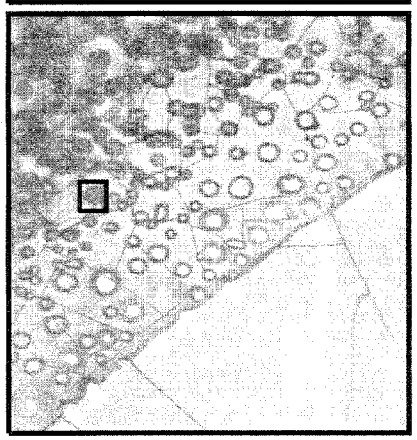

The present inventors have developed novel formulations of insulin based on its fibrillar state, and the experimental results from studies on these novel formulations are presented in the Example hereinbelow. In order to further protect the insulin from the harsh GIT environments, as well as to target it to the intestinal mucosa, the present inventors developed two types of particles that contain phospholipids, albeit with differences in composition and quantities, and for targeting both utilize hyaluronan, that was shown to have muco-adhesive properties in the intestine (Sandri et al., 2004; and Peer et al., 2003).

One type of particles are coated insulin fibrils, where the fibrils dictate the particle structure. The phospholipids coat is composed of phosphatidyl choline (PC) and phosphatidyl ethanolamine (PE) at molar ratios of 90:10, with some of the PE conjugated to hyaluronan.

In the second type of particles, the insulin fibrils are encapsulated in a carrier recently developed in the laboratory of the present inventors group (WO 03/015755; Peer at al., 2004, which are incorporated herein by reference). In this type of particle, which has been named gagomers, the shell of the particle is composed of hyaluronan and its interior contains clusters of a PE (some of which are covalently linked to the shell material, and water). Properties of this formulation, which has been named insulin-gagomers, arise from attributes of both the particles and the insulin fibrils.

Protein fibrillation is a well-recognized phenomena, in both endogenous and exogenous proteins. Even though the dominant overall feature, i.e., that the given protein exists in the form of fibrils, is the same, in terms of structural details and activities however, not all protein fibrils are the same. Moreover, as will be discussed below, for both endogenous and exogenous proteins, fibrillation is usually considered highly detrimental and to be avoided at all costs. Yet, as the present inventors have surprisingly discovered, which is supported by molecular, in vitro and in vivo data as presented in the Example hereinbelow, if handled properly, protein fibrillation can be turned into a positive effect with a wide-scope impact.

For endogenous proteins, the detrimental effects of fibrillation are self-evident, as the phenomena is associated with severe diseases. Noted (but by no means all-inclusive) cases include Alzheimer's and other types of dementia, Parkinson's, Huntington's, ALS, Prion diseases, Type II diabetes, and others (Aigelsreiter et al., 2007; and Eisenberg et al. 2006).

For exogenous proteins used in basic research, fibrillation is highly undesirable as the entity to be studied is the native (active where relevant) protein. When exogenous proteins are developed as therapeutic agents (i.e., "therapeutic proteins"), the consequences of protein fibrillation constitute a far-reaching paradigm that may undermine their clinical application. A hydrated (non-lyophilized) protein has to be stored and kept in its native form, which is a difficult task to achieve due to energetic considerations (Klibanov et al., 2004; and Gazit, 2002). Proteins tend to aggregate, precipitate out of solution, undergo conformational changes that may be irreversible, including loss of function, and adhere to the containers in which they are held (Chi et al., 2003). In order to keep the protein in its native form in solution, there is a need to lower the entropy in the solution. A common approach is to add to the protein of interest to other proteins such as serum albumin or protamine (Defelippis et al., 2006). Another approach is to add specific ions, for example, the traditional use of $Zn^{2+}$ in insulin solutions (Brange et al., 1992; and Richards et al., 1998). Yet, apart from making the product more complex and increase its costs, the means discussed above (salts and/or other proteins) are only a partial kinetic solution and do not truly resolve the root of the problem (i.e., energetics) by thermodynamic means. Furthermore, fibrillation of therapeutic proteins may continue after their administration, aggravating the situation.

In the present invention, the present inventors have taken a novel approach by re-examining fibrillation in therapeutic proteins which is, in a way, "turning the tables" on the phenomena, from detrimental to desirable. The concept is to deliberately drive fibrillation of the therapeutic protein, in the course of making the formulation, to provide the desirable thermodynamic stability to the therapeutic protein. By reaching maximal possible aggregation ex vivo, further aggregation in vivo would be avoided. The crucial issue is that there will be dissociation into monomers in vivo, and that the released monomers will be therapeutically active.

In the Example hereinbelow, the present inventors have provided proof of concept (molecular, in vitro and in vivo experimental data) and actual reduction to practice, drawn from insulin fibrillation, driven under specific conditions. In that respect, it should be noted that there is also support for active monomers coming off (dissociating from) insulin fibrils (Brange et al., 1997). This approach to deliberately generate fibrillation that yields active monomers in vivo can also be applied to other therapeutic proteins such as growth hormones, interferons, G-CSF, erythropoietins, IL2, tPA and others (Schellekens, 2004). Accordingly, the present invention provides a pharmaceutical composition that is preferably adapted for orally delivering a therapeutic protein, which is active in a soluble monomeric form but not sufficiently stable to passage through the gastro-intestinal tract, in an insoluble form that protects the therapeutic protein in the harsh environment of the gastro-intestinal tract while allowing active soluble monomers to dissociate and be released in active form. However, the pharmaceutical composition is not limited to being adapted for oral administration; it can be adapted to other routes of administration, including but not limited to transdermal, subcutaneous, intradermal, intramuscular, intra-articular, etc. The pharmaceutical composition of the present invention includes a pharmaceutically acceptable, carrier, diluent, excipient or auxiliary agent along with an active ingredient in the form of fibrils or insoluble aggregates of a therapeutic protein either encapsulated with lipidated glycosaminoglycan, coated with a multi-layer of lipids and lipid-glycosaminoglycan conjugates, or present as unencapsulated and uncoated fibrils and insoluble aggregates.

One preferred embodiment of the pharmaceutical composition of the present invention is where the fibrils or insoluble aggregates of a therapeutic protein is encapsulated in a lipidated glycosaminoglycan particle (which is insoluble in an aqueous environment), which includes the reaction product of at least one glycosaminoglycan with at least one lipid having a primary amino group.

A second preferred embodiment of the pharmaceutical composition of the present invention is where the fibrils or insoluble aggregates of a therapeutic protein is coated with a multi-layer of at least two lipids and conjugates of one of the at least two lipids and at least one glycosaminoglycan.

A third preferred embodiment of the pharmaceutical composition of the present invention is where the fibrils and insoluble aggregates of a therapeutic protein as active ingredient is present as unencapsulated and uncoated fibrils (plain fibrils) or insoluble aggregates.

The therapeutic protein in insoluble fibrillar or aggregate form as active ingredient in the pharmaceutical composition is preferably insulin, more preferably human insulin when the subject in need thereof to be treated is human. The forms of insulin that are comprehended as the preferred therapeutic protein are all forms defined and disclosed in WO 03/030829, incorporated herein by reference, that are suitable for forming insoluble fibrils or aggregates thereof. It should be appreciated by those of skill in the art that the therapeutic protein may include, but are not limited to, growth hormones, interferons, G-CSF, other cytokines, erythropoietins, IL-2 and other interleukins, tissue plasminogen activator, etc., in which deliberate generation of fibrillation that would yield active monomers in vivo may be applied. Based on the guidance in generating insoluble fibrils of insulin as exemplified in the Example hereinbelow, those of ordinary skill in the art, with only routine experimentation, would be able to find for each therapeutic protein, if suitable, the specific conditions under which insoluble fibrils can be generated.

Lipidated glycosaminoglycan particles, also termed "gagomers", are bioadhesive biopolymers prepared by reacting at least one glycosaminoglycan with at least one lipid, preferably a phospholipid such as phosphatidylethanolamine (PE), more preferably dilauryl phosphatidylethanolamine (DLPE) or dipalmitoyl phosphatidylethanolamine (DPPE) which differ in chain length, to crosslink the carboxylic acid groups in the glycosaminoglycan with a primary amine in the lipid. Preferably, a coupling agent of the carbodiimide type that forms a covalent bond between carboxyl residues of the glycosaminoglycan and the primary amine of the lipid is used for the crosslinking. The glycosaminoglycan in the gagomer particles is a major structural component forming the shell and surface of the gagomer.

A unique feature of the gagomer technology discovered by the present inventors is that these particles, by virtue of their internal lipid regions, provide an environment for encapsulation of insoluble fibrils or aggregates of therapeutic proteins. Gagomer particles therefore have the advantageous ability to perform as a drug delivery system, preferably an oral drug delivery system for therapeutic proteins in insoluble fibrillar or aggregate form. The insoluble fibrils or aggregates of therapeutic proteins are encapsulated in gagomer particles with high efficiency to form the protein drug delivery system according to the present invention. The resultant formulations thus perform as sustained release drug depots which provide stability to the therapeutic protein in the gastro-intestinal tract.

At least when the therapeutic protein is insulin, the size of the lipidated glycosaminoglycan particles encapsulating fibrils of insulin in the pharmaceutical composition of the present invention is in the range of about 10 to 100 microns. This size range is preferred for encapsulating other therapeutic proteins as well.

Although naturally-occurring glycosaminoglycans are preferred in the pharmaceutical composition of the present invention, either in the gagomers or in the multi-layer lipid and lipid-glycosaminoglycan conjugate coating, in order to avoid problems with immunogenicity and toxicity, synthetic glycosaminoglycans can also be used, as well as natural, synthetic, or semi-synthetic molecules, including but not limited to chondroitin, hyaluronic acid, glucuronic acid, iduronic acid, keratan sulfate, keratin sulfate, heparan sulfate, dermatin sulfate, and fragments, salts, and mixtures thereof. The term "glycosaminoglycan" as used herein further encompasses salts and free acids of glycosaminoglycan as well as glycosaminoglycans that have been chemically altered (but not partially hydrolyzed), yet retain their function. These modifications include, but are not limited to, esterification, sulfation, polysulfation, and methylation. Using hyaluronic acid (HA) as an example, its hyaluronate salts include sodium hyaluronate, potassium hyaluronate, magnesium hyaluronate, and calcium hyaluronate.

Natural sources of glycosaminoglycans include both plant and animal sources, i.e., beechwood trees and forms of animal cartilage, including shark cartilage, bovine trachea, whale septum, porcine nostrils, and mollusks such as *Perna canaliculus* and sea cucumber.

The glycosaminoglycans are used at sizes obtained when they are purified from their biological sources, and that have not been subjected to chemical and/or biological degradation. For example, for hyaluronic acid, this corresponds to a range of about $1 \times 10^5$ to about $1 \times 10^7$ daltons.

In the second preferred embodiment of the pharmaceutical composition according to the present invention, the insoluble fibrils or aggregates of a therapeutic protein are coated with a multi-layer of at least two lipids and conjugates of one of the lipids and at least one glycosaminoglycan. Preferably, the at least two lipids is a mixture of phosphatidyl choline, e.g., high purity (Phospholipon 100) soybean phosphatidyl choline (PC), and another phospholipid such as dipalmitoyl phosphatidyl ethanolamine (DPPE), dilauryl phosphatidyl ethamolamine (DLPE) and phosphatidyl ethanolamine (PE), most preferably PE. The at least one glycosaminoglycan can be any suitable glycosaminoglycan, most preferably hyaluronan (HA). The multi-lamellar bioadhesive liposomes (MLV) used as the preferred starting material in the Example hereinbelow are described in U.S. Pat. No. 5,401,511 and Peer et al. (2000), which references are incorporated herein by reference. In the multi-lamellar liposomes used as starting material to coat fibrils or aggregates of a therapeutic protein, the glycosaminoglycan is positioned at the surface of the liposomes, bound covalently to lipids in the outer leaflet of the outermost lipid bilayer.

The pharmaceutical composition of the present invention can be used to treat an indication, i.e., a pathological condition, in a subject in need thereof. The term "subject" as used herein is taken to include humans and other mammals such as cattle, sheep, pigs, goats, dogs, cats, rats, mice, etc., as well as animals including amphibians, birds, reptiles and fish. Humans however are the preferred subjects.

Indications of pathological conditions suitable for treatment with the pharmaceutical composition of the present invention include any indication for which a therapeutic protein in active soluble form is effective for treatment. Examples include, but are not limited to, cancer, bacterial and fungal infections including those secondary to trauma such as burns, infections caused by parasites or viruses, wound healing, inflammation, autoimmune diseases or disorders, etc. In one aspect of the present invention, the pharmaceutical composition of the present invention is used to treat diabetes by orally administering to a subject in need thereof an effective amount of the pharmaceutical composition, where the encapsulated or coated fibrils or the unencapsulated and uncoated plain fibrils are insulin fibrils. The present invention also provides an improved method for treating a subject suffering from an indication/pathological condition which involves administering to the subject an effective amount of the pharmaceutical composition of the present invention, where the therapeutic protein is encapsulated in gagomers, coated with a multi-layer of lipids and lipid-glycosaminoglycan conjugates, or present as uncapsulated and uncoated plain fibrils or insoluble aggregates to treat the indication/pathological condition. In the case of the preferred therapeutic protein embodiment of insulin, the indication/pathological condition is diabetes.

Therefore, one aspect of the present invention is an improvement over current methods for delivering to a subject in need of treatment for a particular indication a soluble therapeutic protein that is effective for treating that indication, the improvement being that the therapeutic protein can now be administered to the subject, preferably orally, in the form of fibrils or insoluble aggregates, with or without being encapsulated or coated, to improve protein stability either over prolonged periods, such as in long-term therapy with implanted or external dosing/drug delivery devices (e.g., insulin pump or transdermal patches) or passage in a harsh environment such as in the gastro-intestinal tract. The therapeutic protein in insoluble fibrillar or aggregate form in the pharmaceutical composition of the present invention would also have an advantage of stability during storage (shelf-life) as would also be appreciated by those of skill in the art.

The pharmaceutical composition according to the present invention is preferably administered orally but may also be administered by another suitable route, including parenteral, e.g., subcutaneous, intravenous, topical, intramuscular, intraperitoneal, transdermal, rectal, vaginal, intranasal or intraocular. Alternatively or concomitantly, administration may be by the oral route. Oral routes of administration are understood to include buccal and sublingual routes of administration.

Parenteral administration can be by bolus injection or by gradual perfusion over time. Parenteral administration is generally characterized by injection, most typically subcutaneous, intramuscular or intravenous.

Topical formulations composed of the active ingredient of the pharmaceutical composition of the present invention, penetration enhancers, and other biologically active drugs or medicaments may be applied in many ways. A liquid formation can be applied dropwise, from a suitable delivery device, to the appropriate area of skin or diseased skin or mucous membranes and rubbed in by hand or simply allowed to air dry. A suitable gelling agent can be added to the liquid formulation and the preparation can be applied to the appropriate area and rubbed in. For administration to wounds or burns, the active ingredient may be incorporated into dosage forms such as oils, emulsions, and the like. Such preparations may be applied directly to the affected area in the form of lotions, creams, pastes, ointments, and the like.

Alternatively, the topical liquid formulation can be placed into a spray device and be delivered as a spray. This type of drug delivery device is particularly well suited for application to large areas of skin affected by dermal pathologies, to highly sensitive skin or to the nasal or oral cavities. Optionally, the pharmaceutical composition may be administered in the form of an ointment or transdermal patch.

The pharmaceutical composition of the present invention may also be administered by other routes which optimize uptake by the mucosa, e.g., vaginal (especially in the case of treating vaginal pathologies), rectal and intranasal routes of administration. Furthermore, the pharmaceutical composition may be adapted for delivery through mucosal tissue or epithelia. If administered intranasally, the pharmaceutical composition will typically be administered in an aerosol form, or in the form of drops. This may be especially useful for treating lung pathologies.

Suitable formulations can be found in A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds $7^{th}$ ed., Lippincott, Williams, & Wilkins; and Handbook of Pharmaceutical Excipients (2000) A. H. Kibbe et al., eds., 3rd ed. Amer. Pharmaceutical Assoc. each of which is incorporated herein by reference.

Depending on the intended mode of administration, the composition used may be in the form of solid, semi-solid or liquid dosage forms, such as for example, tablets, suppositories, pills, capsules, powders, liquids, suspensions, or the like, preferably in unit dosage forms suitable for single administration of precise dosages. The pharmaceutical composition of the present invention and a pharmaceutically acceptable diluent, carrier, excipient, adjuvant, or auxiliary agent. It is preferred that the pharmaceutically acceptable carrier be one which is chemically inert to the active therapeutic protein and which has no detrimental side effects or toxicity under the conditions of use. The choice of carrier is determined partly by the particular active ingredient, as well as by the particular method used to administer the composition. Accordingly, there are a wide variety of suitable formulations of the pharmaceutical compositions of the present invention.

Suitable excipients are, in particular, fillers such as saccharides (e.g., lactose or sucrose, mannitol, sorbitol, etc.) cellulose preparations and/or calcium phosphates (e.g., tricalcium phosphate, calcium hydrogen phosphate, etc.) as well as binders such as starch paste using, for example, maize starch, wheat starch, rice starch, potato starch, gelatin, tragacanth, methylcellulose, hydroxypropylmethylcellulose, sodium carboxymethylcellulose, and/or polyvinyl pyrrolidine.

Injectable formulations for parenteral administration can be prepared as liquid suspensions, solid forms suitable for solution or suspension in liquid prior to injection, or as emulsions. Suitable excipients are, for example, water, saline, dextrose, glycerol, ethanol or the like. In addition, if desired, the pharmaceutical composition to be administered may also contain minor amounts of non-toxic auxiliary agents such as wetting or emulsifying agents, pH buffering agents and the like, such as for example, sodium acetate, sorbitan monolaurate, triethanolamine oleate, etc.

Aqueous injection suspensions may also contain substances that increase the viscosity of the suspension, including, for example, sodium carboxymethylcellulose, sorbitol, and/or dextran. Optionally, the suspension may also contain stabilizers.

The parenteral formulations can be present in unit dose or multiple dose sealed containers, such as ampules and vials, and can be stored in a freeze-dried (lyophilized) condition requiring only the addition of the sterile liquid carrier, e.g., water, for injections immediately prior to use. Extemporaneous injection suspensions can be prepared from sterile powders, granules, and tablets of the kind previously described.

For oral administration, a pharmaceutically acceptable, non-toxic composition is formed by the incorporation of any of the normally employed excipients, such as, for example, mannitol, lactose, starch, magnesium stearate, sodium saccharine, talcum, cellulose, sodium crosscarmellose, glucose, gelatin, sucrose, magnesium carbonate, and the like. Such compositions include suspensions, tablets, dispersible tablets, pills, capsules, powders, sustained release formulations and the like. Formulations suitable for oral administration can consists of liquid suspensions such as effective amounts of the drug encapsulating gagomer particles suspended in diluents such as water, saline, or orange juice; sachets, lozenges, and troches, each containing a predetermined amount of the active ingredient as solids or granules; powders, suspensions in an appropriate liquid; and suitable emulsions. Liquid formulations may include diluents such as water and alcohols, e.g., ethanol, benzyl alcohol, and the polyethylene alcohols, either with or without the addition of a pharmaceutically acceptable surfactant, suspending agents, or emulsifying agents.

When the composition is a pill or tablet, it will contain, along with the active ingredient, a diluent such as lactose, sucrose, dicalcium phosphate, or the like; a lubricant such as magnesium stearate or the like; and a binder such as starch, gum acacia, gelatin, polyvinylpyrolidine, cellulose and derivatives thereof, and the like.

Tablet forms can include one or more of lactose, sucrose, mannitol, corn starch, potato starch, alginic acid, microcrystalline cellulose, acacia, gelatin, guar gum, colloidal silicon dioxide, crosscarmellose sodium, talc, magnesium stearate, calcium stearate, zinc stearate, stearic acid, preservatives, flavoring agents, pharmaceutically acceptable disintegrating agents, moistening agents, and pharmacologically compatible carriers.

Capsule forms can be of the ordinary hard- or soft-shelled gelatin type containing, for example, surfactants, lubricant, and inert fillers, such as lactose, sucrose, calcium phosphate, and corn starch.

Lozenge forms can contain the drug encapsulating gagomer particles in a carrier, usually sucrose and acacia or tragacanth, as well as pastilles comprising the active ingredient in an inert base such as gelatin or glycerin, or sucrose and acacia.

In determining the dosages of the pharmaceutical composition, the dosage and frequency of administration is selected in relation to the pharmacological properties of the specific active ingredients. Normally, at least three dosage levels should be used. In toxicity studies in general, the highest dose should reach a toxic level but be sublethal for most animals in the group. If possible, the lowest dose should induce a biologically demonstrable effect. These studies should be performed in parallel for each compound selected.

Additionally, the $ED_{50}$ (effective dose for 50% of the test population) level of the active ingredient (therapeutic protein in the pharmaceutical composition) in question should be one of the dosage levels selected, and the other two selected to reach a toxic level. The lowest dose is that dose which does not exhibit a biologically demonstrable effect. The toxicology tests should be repeated using appropriate new doses calculated on the basis of the results obtained.

Young, healthy mice or rats belonging to a well-defined strain are the first choice of species, and the first studies generally use the preferred route of administration. Control groups given a placebo or not treated are included in the tests. Tests for general toxicity, as outlined above, should normally be repeated in another non-rodent species. Studies may also be repeated using alternate routes of administration.

Single dose toxicity tests should be conducted in such a way that signs of acute toxicity are revealed and the mode of death determined. The dosage to be administered is calculated on the basis of the results obtained in the above-mentioned toxicity tests. It may be desired not to continue studying all of the initially selected compounds.

Data on single dose toxicity, e.g., $LD_{50}$, the dosage at which 50% of the experimental animals die, is to be expressed in units of weight or volume per kg of body weight and should generally be furnished for at least two species with different modes of administration. In addition to the $LD_{50}$ value in rodents, it is desirable to determine the highest tolerated dose and/or lowest lethal dose for other species, i.e., dog and rabbit.

When a suitable and presumably safe dosage level has been established as outlined above, studies on the chronic toxicity of the active ingredient of the pharmaceutical composition, its effect on reproduction, and potential mutagenicity may also be required in order to ensure that the calculated appropriate dosage range will be safe, also with regard to these hazards.

Pharmacological animal studies on pharmacokinetics revealing, e.g., absorption, distribution, biotransformation, and excretion of the active ingredient and metabolites are then performed. Using the results obtained, studies on human pharmacology are then designed.

Studies of the pharmacodynamics and pharmacokinetics of the active ingredient, formulated in a suitable pharmaceutical composition, in humans should be performed in healthy subjects using the route of administration intended for clinical use, and can be repeated in patients. The dose-response relationship when different doses are given, or when several types of conjugates or combinations of conjugates and free compounds are given, should be studied in order to elucidate the dose-response relationship (dose vs. plasma concentration vs. effect), the therapeutic range, and the optimum dose interval. Also, studies on time-effect relationship, e.g., studies into the time-course of the effect and studies on different organs in order to elucidate the desired and undesired pharmacological effects of the drug, in particular on other vital organ systems, should be performed.

The pharmaceutical composition of the present invention is then ready for clinical trial to compare the efficacy of the active ingredient to existing therapy. A dose-response relationship to therapeutic effect and side effects can be more finely established at this point.

The amount of the active ingredient in the pharmaceutical composition of the present invention to be administered to any given patient must be determined empirically, and will differ depending upon the condition of the patients. Relatively small amounts of the pharmaceutical composition can be administered at first, with steadily increasing dosages if no adverse effects are noted. Of course, the maximum safe toxicity dosage as determined in routine animal toxicity tests should never be exceeded.

Pharmaceutical compositions within the scope of the present invention include all compositions wherein the active ingredient is contained in an amount effective to achieve its intended purpose. While individual needs vary, determination of optimal ranges of effective amounts of each compound is within the skill of the art. The dosage administered will depend upon the age, health, and weight of the individual recipient thereof as well as upon the nature of any concurrent treatment and the effect desired. Typical dosages include 0.01 to 100 mg/kg body weight. The preferred dosages are in the range of about 0.1 to 100 mg/kg body weight. The most preferred dosages are in the range of about 1 to 50 mg/kg body weight.

The preparation of the protein drug delivery system of the present invention is simple and cost-effective. With regard to gagomers, the principles of gagomer preparation are to dissolve the lipid in an organic solvent and evaporate it to dryness in a manner that forms a thin lipid film, which is then hydrated in a basic buffer, usually borate buffer at pH 9. Alternatively, the lipid can be hydrated directly in an appropriate basic buffer at a temperature above the lipid's Tm. The glycosaminoglycan is dissolved separately in an acidic aqueous phase and activated by a water-soluble coupling agent such as a carbodiimide. The hydrated lipid film and the aqueous solution of the activated glycosaminoglycan are brought together and the system is maintained in a basic pH buffer for the covalent bonding to take place.

Two basic types of gagomers may be synthesized: low lipid to glycosaminoglycan ratio (1:1, w/w), denoted LLG, and high ratio of lipid to glycosaminoglycan (5:1 to 20:1, w/w), denoted HLG. By changing specific steps in the preparation, the outcome can be directed to form micro- or nanoparticles.

The gagomers formed are lyophilized (freeze-dried) in a salt-free buffer which is capable of being vaporized during lyophilization so that the lyophilized powder of gagomers are salt-free and buffer-free, and then rehydrated with an aqueous solution of a therapeutic protein of interest. A preferred embodiment of this salt-free buffer capable of being vaporized is an ammonium bicarbonate buffer.

Unlike other particulate carriers such as liposomes, there is no need to add protective agents (cryoprotectants such as sugars) to the gagomers prior to lyophilization, in order to enhance long-term storage and stability of the preparations. The gagomers have intrinsic cryoprotection provided by the glycosaminoglycan, i.e., hyaluronan (hyaluronic acid).

Once the gagomers have been lyophilized, they can be stored for extended periods of time until they are to be used. The appropriate temperature for storage will depend on the lipid formulation of the gagomers and temperature sensitivity of encapsulated materials. Preferably, the temperature is stored at about −18° C.

When the lyophilized gagomers are to be used, rehydration is accomplished by simply adding to the gagomers an aqueous solution containing the therapeutic protein either already in fibrillar or aggregate form or under appropriate conditions such that when encapsulated within the gagomers, the therapeutic protein will readily undergo fibrillation or aggregation, and allowing them to rehydrate and capture the therapeutic protein that was mixed in. This rehydration can be performed at room temperature or at other temperatures appropriate to the composition of the gagomers and their encapsulated therapeutic protein.

The gagomers (lipidated glycosaminoglycans) are preferably prepared by covalently binding a lipid having at least one primary amino group, preferably a phospholipid, more preferably a phosphatidylethanolamine, and most preferably dilauryl or dipalmitoyl phosphatidylethanolamine, to a carboxylic acid-containing glycosaminoglycan, preferably hyaluronan (hyaluronic acid; HA):

Turbidity studies, following light scattering in a spectrophotometer, may be conducted for equal concentrations of soluble hyaluronic acid and of a gagomer prepared from hyaluronic acid and phosphatidylethanolamine to gain insight into whether the synthesis actually yields particulate matter. As expected, over the concentration range tested free hyaluronic acid is soluble, and its solutions do not scatter light. In contrast, the gagomer-containing samples are turbid, the light scattering increasing with the gagomer concentration, making it clear that the gagomers are an insoluble material.

Gagomers are prepared by reacting at least one glycosaminoglycan in the long form, i.e., the gag has not been sliced up into smaller sizes. All glycosaminoglycans, except hyaluronic acid, are naturally in the form of a protein moiety bound covalently to a poly-saccharide moiety. Methods for hydrolyzing the protein-sugar bond, both chemically and enzymatically, are well known to those skilled in the art. In addition, some commercial products are available in which the protein moiety has already been removed.

The glycosaminoglycan is reacted with a lipid which has at least one primary amino group to cross-link the carboxylic residue of the glycosaminoglycan to a primary amine in the lipid. Once this reaction occurs, thermodynamic stability causes the lipids to interact with one another so as to pull the product into a sphere having the glycosaminoglycan on the outside and the lipids on the inside. Self-assembly of the lipid molecules is a critical force in obtaining the gagomer particles. These particles are used to encapsulate the therapeutic protein in the interior of the particles.

According to one aspect of the invention, the method for preparing a gagomer encapsulating insoluble fibrils or aggregates of a therapeutic protein can be generally described as involving:

reacting at least one glycosaminoglycan with at least one lipid containing a primary group to cross-link the carboxylic residue of the glycosaminoglycan with the primary amino group to produce lapidated glycosaminoglycan particles;

removing excess glycosaminoglycan, lipids and reaction by-products from the produced gagomers;

suspending the gagomers in a salt-free buffer which is capable of being vaporized upon lyophilization;

lyophilizing the gagomers to vaporize the buffer, resulting in a salt-free, buffer-free lyophilized powder of the gagomers; and rehydrating the salt-free, buffer-free lyophilized powder of the gagomers with an aqueous solution of a therapeutic protein under conditions for fibrillation or aggregation to encapsulate said therapeutic protein as insoluble fibrils or aggregates in the gagomers.

The protein drug delivery system according to the present invention as gagomers encapsulating insoluble fibrils or aggregates of a therapeutic protein differs from the prior art gagomers encapsulating soluble drugs of WO 03/015755. Using insulin as an example, WO 03/015755 discloses formulating insulin in gagomers under conditions in which insulin forms soluble dimers and hexamers, not insoluble fibrils or aggregates. The differences stem from the formulation/manufacturing process (method of preparation). In the WO 03/015755, the gagomers are not salt- and buffer-free as in the present method for preparation, but rather the gagomers are lyophilized from PBS at neutral pH, and their rehydration is by an aqueous insulin solution so that the rehydration process takes place at neutral pH. In the present invention however, the gagomers are lyophilized from a solution containing only ammonium bi-carbonate, which in the course of lyophilization is converted to the gases $CO_2$ and $NH_3$ that are pumped out, so that the dry lyophized gagomer powder contains no salt and no buffer and is therefore salt-free and buffer-free. The rehdyration with an insulin solution takes place under acidic conditions at pH=2. This makes the gagomer-insulin formulations of the present invention with insulin fibrils encapsulated inside the particles completely different.

The method for the protein drug delivery system according to the second embodiment, where the insoluble fibrils or aggregates are coated with a multi-layer of at least two lipids and conjugates of one of the at least two lipids and the at least one glycosaminoglycan, can be generally described as involving:

reacting at least one glycosaminoglycan with liposomes containing at least two lipids to produce multi-lamellar liposomes having said at least one glycosaminoglycan covalently anchored as a bioadhesive ligand;

removing excess glycosaminoglycan, excess lipids and reaction by-products from the produced multi-lamellar liposomes;

suspending the multi-lamellar liposomes in a salt-free buffer which is capable of being vaporized upon lyophilization; resulting in a salt-free, buffer-free lyophilized powder of multi-lamellar liposomes; and rehydrating the salt-free, buffer-free lyophilized powder of the multi-lamellar liposomes with an aqueous solution of a therapeutic protein under conditions suitable for fibrillation or aggregation to coat the insoluble fibrils or aggregates formed under said conditions with a multi-layer of said at least two lipids and said conjugates of one of said at least two lipids and said at least one glycosaminoglycan.

The at least two lipids are preferably a mixture of phosphatidycholine (PC) and phosphoethanolamine (PE). The at least one glycosaminoglycan is preferably hyaluronan. The salt-free buffer capable of being vaporized upon lyphilization is preferably an ammonium bicarbonate buffer.

The liposomes of PC and PE are first formed and then HA is bound to PE at the surface of the pre-formed liposomes. In the case of insulin, the dry lyophilized powder of lyophilized liposomes is rehydrated with an acidic solution of insulin by incubation at 37° C. in a shaker bath (with shaking). The present inventors believe that the following steps occur (although the present invention is not bound by any particular mechanism). At first, the liposomes are reconstituted in the course of which insulin monomers are encapsulated within the liposomes. The insulin fibrillation starts inside the liposomes, but this is a slow process. At about 24 hours into the incubation, liposomes (with insulin inside) can still be seen. The insulin monomers that undergo the fibrillation process inside the liposomes are aided by two factors, both known to promote the insulin fibrillation, low pH and the ability of the insulin to interact with hydrophobic entities, i.e., the liposomal lipids in this case. Under the conditions used, about 48 hours into the incubation liposomes are no longer seen. At about 96 hours into the incubation, most of the material is already in the form of the coated insulin fibrils, and this process is complete at about 192 hours.

The present inventors believe that along the way (somewhere between about 24 and 48 hours of incubation) the intra-liposomal fibrils become too large to be accommodated inside the liposomes. This leads to bursting of the liposomes, but the lipids (as well as the lipid molecules that were conjugated to hyaluronan on the surface of the liposome) remain attached to the fibrils, thus forming the coat. Upon the bursting of the liposomes, there will be two kinds of "raw materials" for the coat: (1) lipid molecules (phosphatidylcholine (PC) and phosphatidylethanolamine (PE)) and (2) the PE-HA conjugate. In this conjugate, the PE and the HA are bound to each other by a covalent bond. This is a strong bond that will not break when the liposomes are disrupted/burst. For the interaction with the insulin fibrils, the PE-HA conjugate will be part of the coat because its PE component behaves similar to the molecules of PE that have no HA bound to them, and also essentially similar to the PC molecules. Since the HA in the conjugate is covalently attached to PE and the latter is part of the coat, this makes the HA also part of the coat. There are two reasons the lipids remain attached to the insulin fibrils: (1) the hydrophobic interaction between the fibrils and the lipids; and (2) the bits and pieces of the lipids have two options, either to remain associated with the fibrils or to float as lipids alone in the aqueous media. The option of remaining attached to the insulin fibrils is preferred on the grounds of thermodynamic/energetic stability.

The particles of encapsulated or coated protein fibrils or aggregates can be used as a scaffold for tissue engineering, particularly if structural proteins are employed as the protein fibrils or aggregates encapsulated or coated in the particles.

Having now generally described the invention, the same will be more readily understood through reference to the following examples which are provided by way of illustration and are not intended to be limiting of the present invention.

Example 1

In this study, the molecular, in vitro and in vivo findings on various formulations of insulin fibrils for oral delivery are presented.

Materials and Methods

Materials

Phospholipon 90G (high purity Soybean phosphatidylcholine (SPC) was a kind gift from Nattermann Phospholipid GmbH (Cologne, Germany). Dipalmitoyl phosphatidylethanolamine (DPPE), Insulin from Bovine pancreas (28.7 IU/mg), Pepsin from porcine stomach mucosa (1.100 U/mg protein.), Pancreatin from porcine pancreas (4×USP), N-Ethyl-N'-(3-dimethylaminopropyl)carbodiimide hydrochloride (EDC), Streptozotocin (STZ), Pronase (6 U/mg), Thioflavin-S, 17-β Estradiol, Hydrocortison, Human Transferrin and Sodium Selenite were from Sigma Chemical Co. (St. Louis, Mo.) Hyaluronan (HA) 1.2 KDa was a kind gift from Genzyme (Cambridge, Mass.). FITC-tagged Insulin was from Invitrogen Corporation (CA, USA). Human recombinant insulin was from Boehringer-Mannheim (Germany). Dulbecco's modified Eagle's medium (DMEM) containing 5% Heat-inactivated Fetal Bovine Serum (FBS), 1% MEM-Eagle Non essential amino acids (×100), 1% L-glutamine, 1% Penicillin (10000 unit/ml)+Streptomycin (10 mg/ml)+ Nystatin (1250 unit/ml) solution, and 0.25% Trypsin-EDTA solution were from Biological Industries (Beit Haemek, Israel). All other materials were of analytical grade. ICR male mice were purchased from Harlan Laboratories (Jerusalem, Israel).

Ultracentrifugation was performed with a Sorval Discovery M120 SE micro ultracentrifuge, Thermo Fisher Scientific (MA, USA). Lyophilization was performed with a HETO Drywinner 3 (Denmark). Rotary evaporation was performed with a Rotavapor R-205, Buchi Labortechnik AG (Flawil, Switzerland). Fluorescence and light microscopy were performed with a Leica DMRB upright microscope, Leica Microsystems Gmbh (Wetzlar, Germany). Confocal microscopy was performed with a ZEISS LSM 510, Carl Zeiss MicroImaging Gmbh (Gottingen, Germany). The scanning Electron Microscope (SEM) was Jeol 480A (Tokyo, Japan). The Glucose Meter was Roche ACCU-CHEK Go, with compatible Roche ACCU-CHEK Go strips (Basel, Switzerland). Needles for per-oral administrations were from Animal Feeding Needle Straight 18G 1½" from Popper's & sons, Inc. (NY, USA).

Methods

Preparation of the Insulin Fibril Formulations

1a. Plain Insulin Fibrils (Uncoated and Unencapsulated)

Insulin at concentrations ≥1 mg/ml was dissolved in DDW acidified to pH=2 with 1N HCl, and agitated in an incubator at 37° C. for selected time spans. When desired, the initial insulin solution was doped with a trace of FITC-insulin (1:100 v/v). These plain insulin fibrils serve as controls, especially for in vivo studies.

1b. Coated Insulin Fibrils

The starting material was multilamellar bioadhesive liposomes (MLV) in which hyaluronan was the covalently-anchored bioadhesive ligand (BAL), denoted HA-BAL (Peer et al., 2000). Lyophilized powder of buffer-free salt-free HA-BAL were prepared according to previously-described procedures (Peer et al., 2000; and Margalit, 1995) except: ethanol replaced chloroform:methanol mixtures for lipid dissolution, the swelling solution was 0.1M borate buffer at pH 9, and incubation of the dry lipid film was for 2 hours at 65° C., in a shaker bath. A portion of these was set aside as a control and the remainder was taken to surface modification, binding hyaluronan, according to the previously-reported processes (Yerushalmi et al., 1994 and 1998). Briefly, to obtain HA-BAL, HA dissolved in acetate buffer (0.1 M, pH 4.5) at the concentration of 2 mg/ml, was pre-activated by incubation with EDC for 2 hours at 37° C. The pre-activated HA was mixed with the liposome suspension, at the ratio of 1:1 (v/v). The pH was adjusted to 9, and the mixture was incubated for 24 hours under shaking at 37° C. The bioadhesive liposomes were freed from excess materials and by-products by ultracentrifugation (160850×g, 40° C., 40 minutes) followed by several successive washes and re-centrifugations in 100 mM ammonium bi-carbonate buffer at pH=8. Aliquots of 1 ml of the resulting HA-BAL were frozen for 2 hours at −80° C., followed by 24 hours lyophilization. The resultant HA-HAL powders were stored at −18° C. until further use.

The liposome powder was re-hydrated with an aqueous solution of insulin acidified to pH=2 and the process was continued as described in 1a above. When needed, the systems were centrifuged in an ultracentrifuge (conditions as listed above), the supernatant was separated and saved, and the pellets—the coated insulin fibrils—were re-suspended in DDW to be used as is, or lyophilized until further use. The insulin concentration in the pellet was evaluated by subtracting the insulin in the supernatant from the initial insulin concentration, using either absorbance at 280 nm or fluorescence (for the systems containing the trace FITC-insulin) with excitation and emission at 480 nm and at 530 nm, respectively.

1c. Insulin-Gagomer Particles

This was a two-step process. In the first, buffer-free salt-free gagomers were prepared and lyophilized. In the second, the insulin was encapsulated in the gagomers, under conditions that resulted in its fibrillation within the particle.

1ci. Preparation of Buffer-Free Salt-Free Gagomers.

Dipalmitoyl phosphatidylethanolamine (DPPE) was dissolved in ethanol, usually at the concentration of 12 mg/ml at 65° C., until dissolution was complete. Ethanol evaporation and generating a phosphatidylethanolamine (PE) suspension in 0.1M borate buffer at pH 9, was done as described above in 1b for the liposomes, except the borate-lipid suspension was incubated in a shaker bath for 2 hours at 65° C., in a shaker bath. Typical lipid concentration in the basic buffer were 12 mg/ml. Separately, hyaluronan (HA), at a concentration of 2 mg/ml was activated by the crosslinker EDC as described above in 1b. At the end of incubation, the activated HA solution was added to the lipid solution at a ratio of 1:1 (v/v), the pH was corrected back to 9 and the mixture was incubated in a shaker bath for 24 hours at 37° C. The resulting gagomer particles were freed from excess materials and by-products by ultracentrifugation (160850×g, 40° C., 40 minutes) followed by several successive washes and re-centrifugations in 0.1M ammonium bi-carbonate buffer at pH=8. Aliquots of 1 ml of the gagomer suspensions (final gagomer concentrations of 0.6, 1.2 or 12 mg DPPE/ml) were frozen for 2 hours at −80° C., followed by 24 hours lyophilization. The gagomer powders were stored at −18° C. until further use.

1cii: Formulating Insulin-Fibrils Inside the Gagomers.

An aliquot of the gagomer powder was rehydrated back to original pre-lyophilization volumes, with an aqueous solution of insulin acidified to pH=2. The process was continued to completion, as described in 1a and 1b above. Insulin encapsulation efficiency was determined as described in 1b above for the pellets of the coated insulin fibrils, except in the present case the pellet contained the gagomers with their encapsulated insulin load. When needed, insulin-gagomer particles freed of unencapsulated insulin were also lyophilized until further use.

Light, Fluorescent and Confocal Microscopy

2a. Light Microscopy:

The pH of samples from selected systems was raised to 8. Aliquots of 10 µl or 100 µl were pipetted onto a microscope slide glass and covered with a cover glass, or into wells in a 96-well plates, respectively. The plates were taken to a light microscope, as is (for viewing in the hydrated state), or left to dry at 37° C. (for viewing in the dry state). The slides were viewed under ×100 magnitude.

2b. Fluorescent Microscopy:

The pH of samples from selected systems, containing trace FITC-insulin, was raised to pH 8, and 10 µl aliquots were pipetted onto a microscope slide glass and covered with a cover glass. The slides were viewed under a fluorescence microscopy. Excitation and emission were at 480 nm and at 530 nm, respectively. Slides were viewed under ×100 magnitude.

2c. Confocal Microscopy:

The pH of samples from selected systems, containing trace FITC-insulin, was raised to pH 8, and 10 µl aliquots were pipetted onto a microscope slide glass and covered with a cover glass. Excitation and emission were at 480 nm and at 530 nm, respectively. Slides were viewed under ×40 magnitude lens.

Scanning Electron Microscopy (SEM) of Insulin-Gagomer Particles

SEM was performed in the Life Science Inter-department Research Facility Unit (IDRFU) at Tel-Aviv University.

Samples were fixed with 2.5% glutaraldehyde in PBS. They were then washed, dehydrated in graded ethanol solutions, dried from $CO_2$ at critical point. Coated with gold (Polaron SEM coating unit E5100) and examined in a Jeol JSM 840A SEM.

Thioflavin-S (Th-S) Staining

Staining was done according to Carson FL (1990). Acidic insulin fibril solutions were prepared as in 1 above. Samples (at the end of 48 hours of incubation) were pipetted into wells of 96-well plates (100 µL aliquots) and allowed to dry as in 2 above. 200 µL of a 1% aqueous Th-S solution was added to each well. After 3 minutes of incubation the Th-S was aspirated and each well was subjected to 3 successive washes with 200 µL water. The wells were then incubated for 20 minutes with 200 µL of 1% acetic acid. At the end of incubation, the acetic acid was aspirated and each well was washed with water as above, and left to dry. The plate was viewed under a fluorescence microscope, excitation and emission wavelengths were at 450 nm and 480 nm, respectively.

Stability in Proteolytic Environments

Pronase, which is a commercially-available mixture of non-specific proteases operating at physiological pH served to model a hostile proteolytic environment (U.S. Pharmacopoeia 27 NF 22, 2004; and Fischer et al., 2005).

Gagomer insulin powder (containing a trace of FITC-insulin), lyophilized from 1 ml and freed from excess unencapsulated insulin prior to lyophilization, was rehydrated with 1 ml of a 3 mg/ml pronase solution, in PBS pH=7.4. The system was incubated in a shaker bath for 30 minutes at 37° C., at the end of which retention of insulin in the particles was determined as in 1b above.

Stability in Simulated Gastric Fluid (GIF) and Simulated Intestinal Fluid (SIF)

SIF and GIF were prepared according to the USP 27 NF 22 (2004) as follows: (i) 1000 ml GIF contained 2.0 g of sodium chloride (NaCl), 3.2 g of purified pepsin in 7 ml of 32% hydrochloric acid and water, and (ii) 1000 ml SIF contained 6.8 g of monobasic potassium phosphate ($KH_2PO_4$), 77 ml of 0.2N sodium hydroxide (NaOH), 10 g of pancreatin (i.e., amylase, trypsin, lipase, ribonuclease and protease) and water. The pH was adjusted 6.8±0.1 by titration with 0.2 N NaOH or 0.2 HCl, according to need.

Coated fibrillar insulin and insulin-gagomer particles (containing trace FITC-insulin) were prepared and separated from excess un-encapsulated insulin as in 1b and 1c, above. Suspensions of the coated insulin fibrils and of the insulin-gagomers were mixed 1/7 v/v with either SIF or GIF. Typical final doses of the coated insulin fibrils had 0.23 mg/ml insulin and had 14 mg/ml lipid (mostly phosphatidylcholine (PC) and typical final doses of insulin-gagomers had 0.5 mg/ml insulin and 1.7 mg/ml lipid (only PE). The systems were incubated in a shaker bath for 2 hours at 37° C., at the end of which retention of insulin in each type of particles was determined as in 1b above.

Cell Culture Growth and Maintenance

NCI-H2009 cells, originating from human non-small cell lung carcinoma were cultured in with DMEM medium at 37° C. in 5% $CO_2$. The DMEM contained 5% FCS, and was supplemented with 1% antibiotics (penicillin, streptomycin and neomycin), 0.83 µM recombinant human insulin, 10 nM 17-β-estradiol, 10 nM hydrocortisone, 2 mM L-glutamine, 30 nM Na-selanide and 0.01 mg/mL human transferrin.

For a given experiment, 200 µL cells at the density of 104 cells/well were seeded onto 96-well plates, and the experiment was initiated 24 hours later. Upon initiation, the serum-supplemented cell growth media was replaced with a similar media containing reduced serum—3.5% or 1.5% FCS—supplemented with increased insulin doses over the range of 0-50 µM. Termination was 48 hours later and cell viability was determined in each well, using the MTT method.

In-Vivo Studies

7a. Animals

Eight weeks old Male ICR mice were housed in an air-conditioned animal room at 25° C. Animals were on a 12 h/12 h day night regime. All experiments described were approved by the Experimental Animal Research Committee of the Tel-Aviv University, Tel-Aviv, Israel. (Committee approval numbers: L-05-035; L-06-033).

7b. Diabetes Induction and Monitoring

Diabetes was induced with a single i.p. streptozotcin (STZ) injection of 150 mg/kg body. STZ was freshly dissolved in cold 0.05M citrate buffer, pH=4.5. Each animal was weighed before and after STZ injection, the latter daily. Blood glucose levels were determined by withdrawing blood from the tail vein and measuring with the glucose-meter.

7c. Insulin Administration

7c1. Conventional Injection:

Bovine insulin was dissolved in aseptic PBS buffer (100 mM, pH=7.6). 100 μL of Insulin 1.5 IU/kg body, were injected s.c.

7c2. Oral Administration:

100 μL of the desired insulin formulation (or saline) was administered orally, using a gavage needle.

7d. In Vivo Effects of Oral Insulin Administrations and of Controls

At the beginning of each experimental run (t=0), blood samples were collected from each mouse, and assayed for glucose levels. Mice were considered diabetic, and taken to the experiment, only if their blood glucose levels were >400 mg/dl (no prior fasting). The animals were randomized into the following treatments: (1) the test systems—plain, coated or gagomeric insulin fibrils PO (10 IU/mouse); (2) Free Insulin PO (10 IU per mouse); (3) Conventional treatment: Free insulin s.c. (1.5 IU/kg body) and (4) No treatment. Blood glucose levels were also determined at selected time points up to 8 hours. Food was taken away at time=0 and the animals were given access to food for a duration of 20 minutes after the t=4 hours glucose measurement. The animals had access to water for the duration of the experiment.

Results and Discussion

Formation and Structural Characterization of Plain and Coated Insulin Fibrils

1a. Plain Insulin Fibrils

Figure 1C:
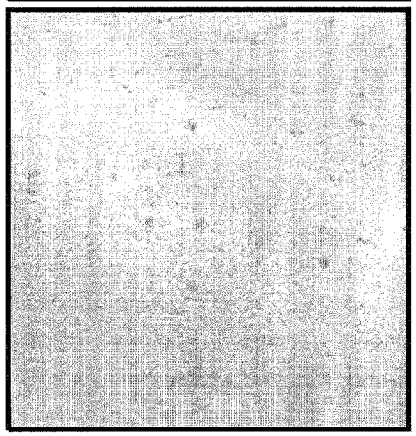

Insulin fibrils play a key role in the novel insulin formulations studied in this Example. Hence the formation and properties of insulin fibrils alone were first characterized and under conditions that were subsequently applied for the novel formulations. It is well-known that under the acidic conditions (pH=2) insulin solutions at concentrations ≥0.2 mg/ml tend to aggregate in a unique fibrillar manner. Factors implicated in the process are of a chemical nature and of a mechanical nature, the former including insulin concentration and electrolyte composition and concentration, the latter including agitation and temperature (Whittingham et al., 2002). Under agitation, at pH=2 and an insulin dose of 5 mg/ml, 24 hours sufficed to generate insulin fibrillation. A typical example, from bovine insulin, is shown in FIG. 1A: The picture is a close-up of a single (but representative) well, where it can be seen that most of the aggregated insulin localizes at the well perimeter, showing the unique structures of insulin fibrils called spherolites (Salman et al., 2006). To further identify these structures, preparations similar to those in FIG. 1A, treated by the specific fibril fluorescent dye Th-S, are shown in FIG. 1B. The pattern of fluorescent staining obtained, clearly indicates that the insulin aggregates are fibrillar. Similar results were obtained with human recombinant insulin.

To assess effects of electrolytes in the system, concentrated insulin fibrils (such as those shown in FIG. 1A, but of human recombinant insulin) were centrifuged from a salt-free aqueous solution at pH=2. The fibrillar content of the supernatant is quite low, as can be seen in FIG. 1C. Increasing the electrolyte concentration by adding PBS (to a final concentration of 10 mM) generated a significant enhancement in fibrillation, as seen in FIG. 1D. It should be pointed out that this is salt rather than pH effect, since both systems (i.e., with and without PBS) were at pH=8.

Figure 1E:
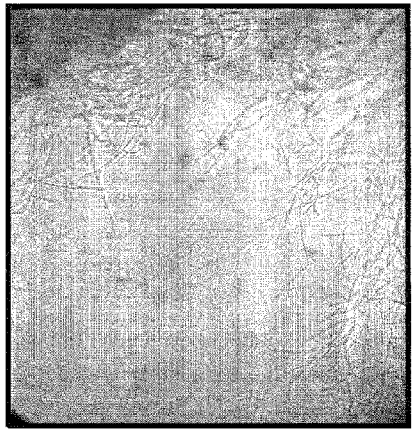
Figure 1B:
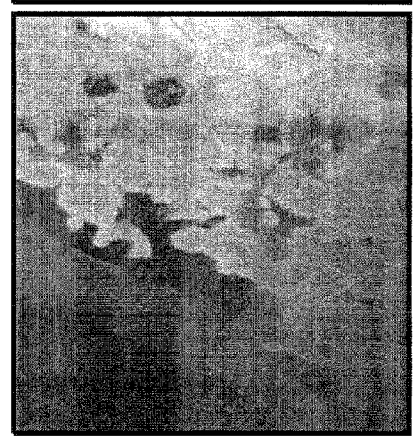
Figure 1D:
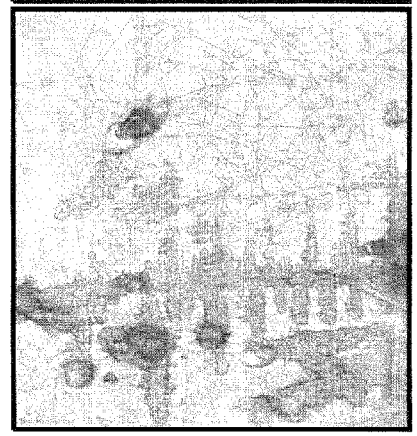
Figure 1F:
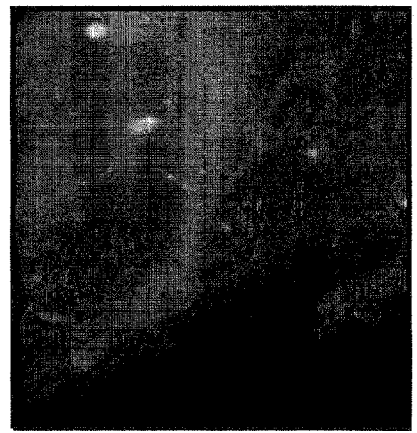

Agitation was not found to be critical for fibrillation, as exemplified by the light and fluorescent microscopies (FIGS. 1E and 1F, respectively). Yet agitation is quite desirable as it otherwise took 2 weeks for the process to come to completion. The phenomena of fibrillation is independent of insulin origins, as reported elsewhere (Brange et al., 1997) and as shown here for bovine and human recombinant insulin. It is the rate of fibrillation that may vary among species. Based on technical considerations, most of the work here was preformed with bovine insulin. Insulin fibrils obtained in DDW acidified to pH=2 (see the methods section for further details) will be referred to as "plain insulin fibrils".

1b. Coated Insulin Fibrils

Although the starting materials for the coated insulin fibrils contain liposomes, there are several distinct differences between the system used here and previous attempts to obtain insulin-encapsulating liposomes (Morishita et al., 2006; and WO 03/030829). One difference is in the raw materials; the other cases used conventional liposomes are used and hence lipids only, whereas in this Example hyaluronan bioadhesive liposomes hence both lipids and the hyaluronan-DPPE conjugates are present. Another difference is in the end goal of insulin form; in the other cases, efforts were made to stay away from insulin fibrillation focusing mostly on monomeric insulin, or at most the well-known insulin hexamers. In this study case, as already indicated, the fibrillar insulin form was deliberately sought. A third critical difference is in the method and process of formation; in the other cases, insulin was incorporated into the liposomes applying the traditional method by which the insulin is in the swelling solution reacted with the thin lipid film. In this Example, the method previously developed in the laboratory of the present inventors, in which lyophilized powders of drug-free liposomes are rehydrated with an aqueous solution of the drug intended for encapsulation (Peer et al., 2000), was used. In the present case, lyophilized powders of pre-formed drug-free salt-free hyaluronan bioadhesive MLV were rehydrated with aqueous insulin under conditions for fibrillation. As will be shown below, these critical differences resulted in the coated insulin fibrils according to the present invention that are clearly a different entity than insulin-encapsulating liposomes.

Figure 2A:
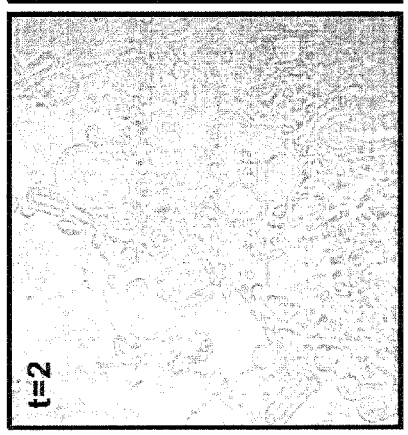
FIGS. 2A-2H are light and fluorescence microscopy images of coated insulin fibrils (bovine insulin, containing trace FITC-insulin). Magnification was ×100.
Figure 2C:
Figure 2E:
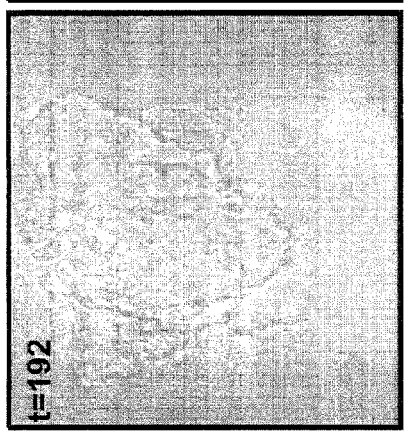
Figure 2G:
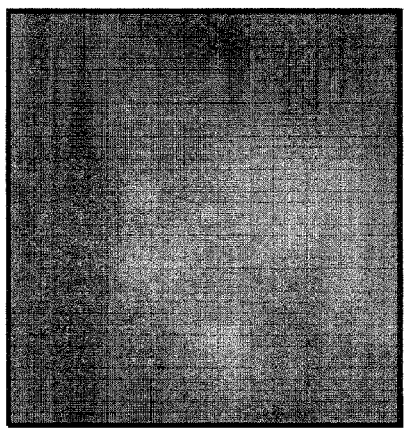
Figure 2B:
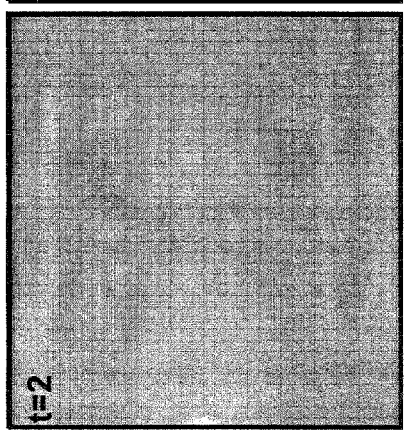
Figure 2D:
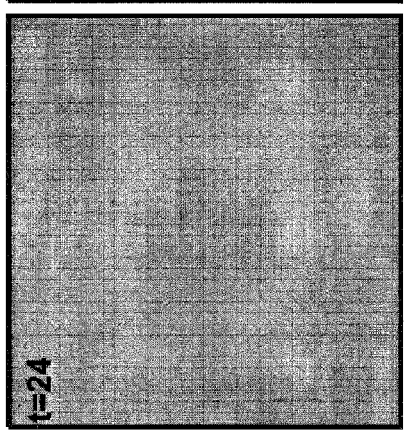
Figure 2F:
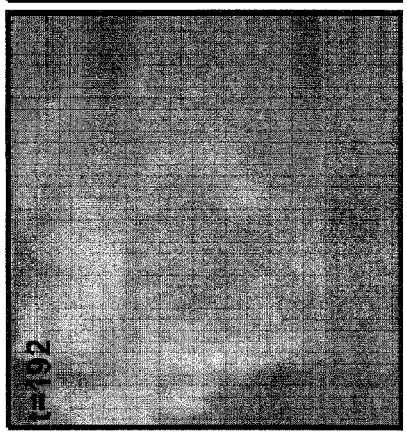
Figure 2H:
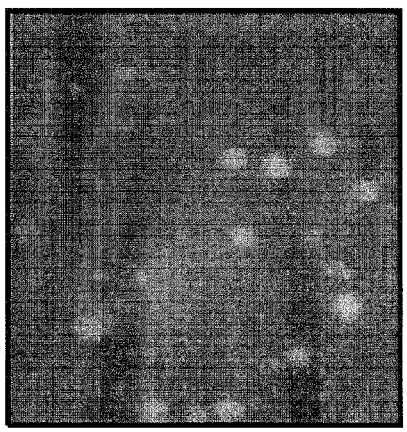
Figure 3C:
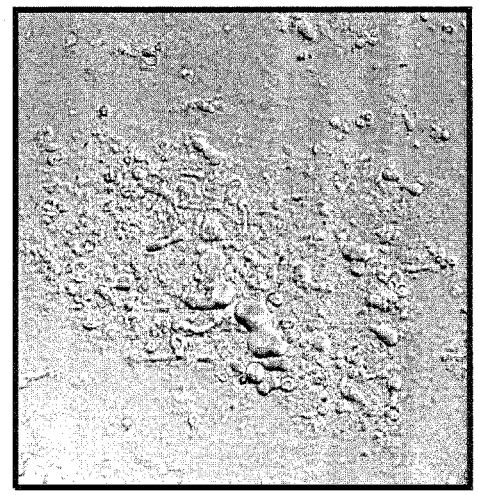
FIGS. 3A-3C are confocal microscopy images of coated insulin fibrils similar to those in FIGS. 2A-2H, after 24 hours of incubation, and separation from excess insulin, Magnification was ×40. Excitation and emission were at 480 nm and at 530 nm, respectively. The scale bar (bottom left) is 5 µm.
Figure 3B:
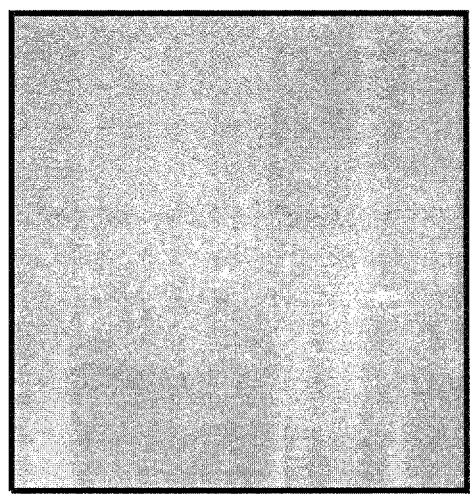
Figure 3A:
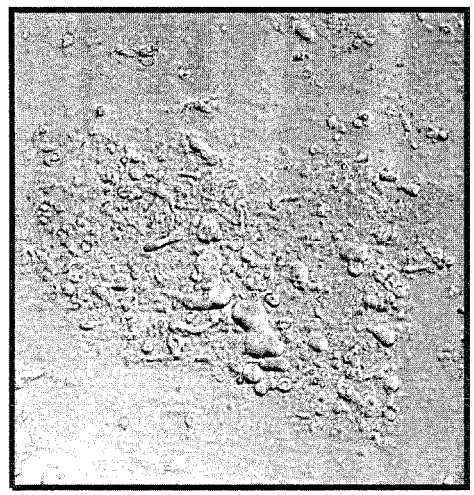

Taking into consideration that insulin fibrils grow with time (Whittingham et al., 2002), as also shown above, incubation of insulin with lyophilized powders of drug-free salt-free gagomers at pH=2, was for 192 hours. Samples were taken for observation at interim time points (2 and 24 hours into the incubation) and upon termination. Typical views under light and fluorescent microscopy, are shown in FIGS. 2A-2F, where the particles (deliberately) were not separated from free insulin prior to viewing. Two hours into the incubation, as seen in FIG. 2A, the structures seen under the light microscope are quite typical for aggregates of drug-free liposomes (MLV). These liposomes, being in the sub-micron range, cannot be seen as individual particles with any details under the level of magnification this type of microscopy affords. The insulin, shown in FIG. 2B, appears at this early time point as a smear over the entire image, implying significant fibrillation but association with the coat materials has not occurred yet. After 24 hours, as seen in the FIGS. 2C and 2D, significant changes have taken place. The liposomal aggregates (FIG. 2C) seem to change shape, concentrating into fewer structures that now cover only part of the viewed field (compared to FIG. 2A), and they also seem to be aligned on "net strings" rather then randomly distributed. Concomitantly, the insulin (FIG. 2D) is no longer randomly distributed as in FIG. 2B. Rather, it is now localized in specific areas that furthermore coincide with those of the particulate structures (compare FIGS. 2C and 2D). These views are similar, and fit with, the results of the same incubation period viewed under the confocal microscope (FIG. 3). Extending the incubation period 8-fold, as shown by FIGS. 2E and 2F, completes the process. Clearly, no liposomal aggregates are seen but rather one big particle (FIG. 2E). Moreover, the insulin (FIG. 2F) is totally associated with this particle, with no free insulin remaining in the system. The liposomal matter, which consists of lipids lipid-hyaluronan conjugates, appears to be bonded to the growing insulin fibrils rather than separated and detached.

Formation and Structural Characterization of the Insulin-Gagomer Particles

Lyophilized powders of drug-free salt-free gagomers were incubated with insulin solutions at pH=2, for 2 and for 48 hours as described under the methods section, and typical results are shown in FIGS. 4A-4F. At 2 hours of incubation, no structural differences are seen in the gagomers (FIG. 4A), yet some insulin clustering (FIG. 4B) with the gagomers is already seen. Extending the incubation to 48 hours shows a dramatic change—the gagomer particles are less aggregated (compare FIGS. 4A to 4C), and the insulin is in discrete particles that coincide with the gagomer particles (compare FIGS. 4C and 4D). A close up look at the same field as in FIGS. 4C and 4D shows the discrete insulin-gagomer particles, some of which seem to be connected with the "strings" that may be insulin fibrils (recall FIGS. 1A-1H).

Figure 5C:
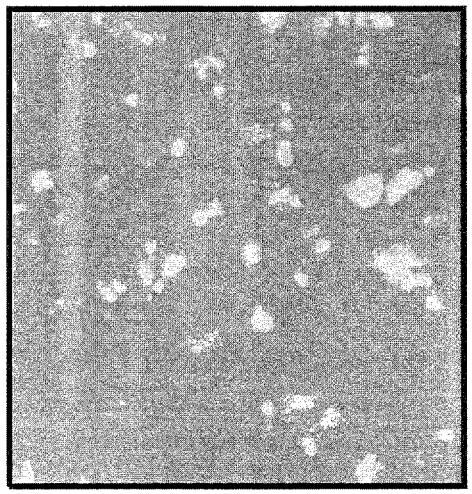
FIGS. 5A-5C are confocal microscopy images of insulin-gagomer particles similar to those in FIGS. 4A-4H, after 24 hours incubation and separation from excess unencapsulated free insulin (magnification ×20). Excitation and emission were at 480 nm and at 530 nm, respectively. The scale bar (bottom left) is 10 µm.
Figure 5B:
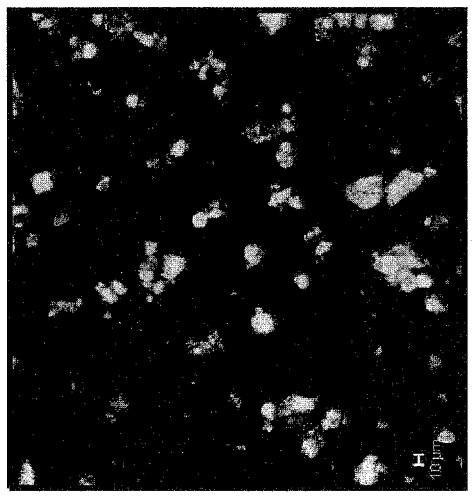
Figure 5A:
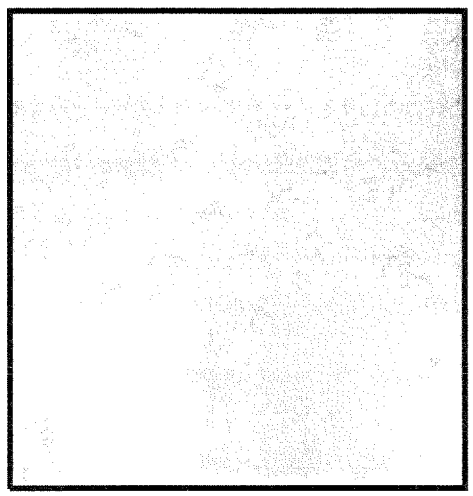

To gain more insight into the insulin-gagomer structures obtained, two additional microscopy approaches, confocal and SEM, were applied. For the samples taken to view under the confocal microscope, incubation of insulin with the gagomer powder was for 24 hours. The insulin-loading gagomers were separated from excess un-encapsulated insulin prior to viewing (see the methods section for further details). The results, exemplified in FIGS. 5A-5C, clearly indicate that 24 hours of incubation suffice to obtain the final product (compare FIGS. 5A-5C to FIGS. 4C-4E). Comparing the view of the particles themselves (FIG. 5A) with those of the insulin alone (FIG. 5B) and the composite of both (FIG. 5C) makes it clear that insulin does not form a halo/shell around the particle. Rather, it fills the entire particle indicating it is loaded within. The fibrils are probably intertwined with the interior gagomer components (i.e., the lipid clusters and some hyaluronan).

Figure 6C:
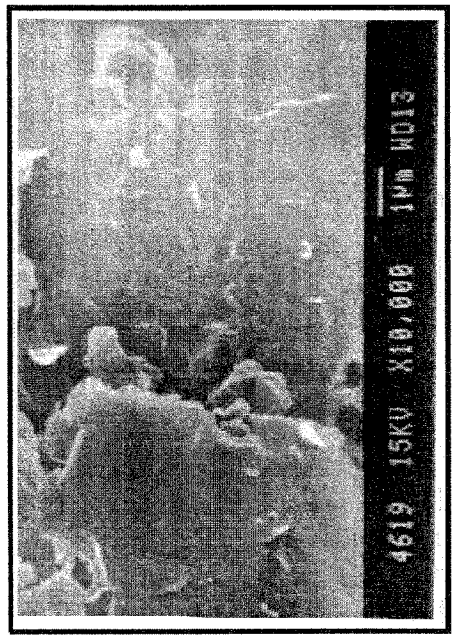
FIGS. 6A-6C are scanning electron microscopy (SEM) of "empty" and of insulin-loaded gagomers. Magnification and scale are listed at the bottom of each picture.
Figure 6B:
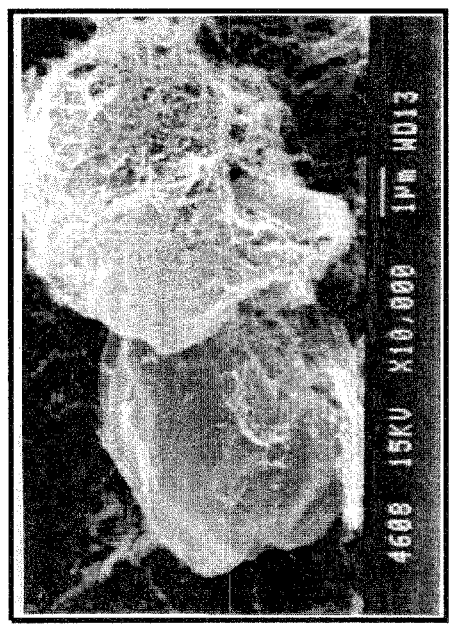
Figure 6A:
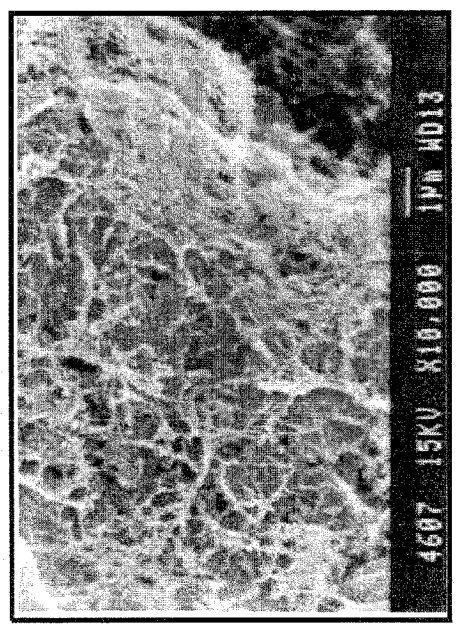

Further refined structural details of the insulin-gagomer particles were obtained by SEM. Insulin-gagomer particles ranged from 10-100 μm (diameter), as shown by examples taken from the lower and higher ends. Both examples (FIGS. 6A and 6B) show insulin fibrils filling the interior of the particle. This is particularly evident by the right-hand particle of FIG. 6B, and by the comparison of the insulin-gagomer (FIG. 6B) to an "empty" gagomer (FIG. 6C). Needless to say, this comparison was done under the same magnification conditions for similar-sized particles. In addition, the "empty" (i.e., encapsulating water alone) gagomers were obtained by rehydration of lyophilized drug-free gagomers, done under identical conditions to those of the insulin-loaded gagomers except the acidic rehydration solution did not contain insulin (see the methods section for further details).

In conclusion, the results from several different microscopic approaches, are in agreement. They demonstrate that insulin-gagomers are a distinct new structural entity which is different from drug-free gagomers, and from mixtures of the two "raw materials" (i.e., insulin and separately drug-free gagomers). These micrographs also show very clearly that the insulin fibrils are within the gagomers.

Insulin Loading Efficiencies in the Gagomers and in the Coated Fibrils.

Insulin loading efficiency inside the gagomers was evaluated over a 20-fold range of gagomer, and over a 10-fold range insulin concentration. Very high loading was obtained, as clearly seen from the results listed in Table 1.

TABLE 1

Efficiency of insulin loading inside gagomers as function of insulin dose and gagomer concentration

| Initial insulin dose (mg/ml) | Insulin loading efficiency (% from initial dose) Gagomer concentration* | | |
|---|---|---|---|
| | 0.6 | 1.2 | 12 |
| 1 | 90(±9)** | 87(±5) | 64 ± (0.3)*** |
| 3 | Complete**** | | Complete |
| 4 | | | Complete |
| 5 | | Complete | Complete |
| 6 | | Complete | |
| 10 | | Complete | 96(±1) |

*Gagomer concentration is defined by its lipid concentration (mg DPPE/ml)
**Each value is an average of 3-5 batches and the number in parenthesis is the sd
***Insulin incubation with the lyophilized gagomer powder was for 5 hours. In all other cases the incubation was 24 hours.
****Complete indicates the concentration of excess unencapsulated insulin was below detection.

The data also show that over the ranges tested, encapsulation efficiency was not restricted to specific insulin or gagomer doses. The one dominant factor was the incubation time span. Allowing fibrillation and particle organization a time span of 5 hours was not sufficient for complete encapsulation, even though the level obtained, 64%, already quite satisfactory. Under the same conditions—24 hours of incubation and a similar insulin dose range—insulin loading efficiency in the coated fibrils was 48(±9)% (n=9), independent of the specific initial insulin dose (within the test-range of 1-5 mg/ml). Since the concentration of coat materials was the same in all systems, it implies a major role for the lipids and the hyaluronan-lipid conjugates in the formation of these coated insulin fibrils.

Stability in Simulated GIT Environments

A protein formulation designated for in vivo oral administration obviously has to survive the environments along the GIT. Those can be hostile due to pH conditions and to enzyme-catalyzed proteolysis. To gain insight into the stability the fibrillar insulin formulations in this study prior to in vivo testing, use was made of the well-known formulations that simulate those environments in the test tube. The two types of insulin particles—the coated fibrils and the gagomers—freed from excess unencapsulated insulin, were incubated with the selected environments for two hours at 37° C. A qualitative view for insulin-gagomers incubation in GIF, shown in FIGS. 4G and 4H, clearly demonstrates that even in this harsh environment, most of insulin remains within the gagomers, quite similar to equivalent systems not exposed to GIF (FIGS. 4C-4F). The quantitative results—the fractions of the initial insulin load retained at the end of the incubation—are listed in Table 2. Clearly satisfactory stability was obtained for both types of particles, with some advantage for the gagomers.

TABLE 2

Stability of particle-formulated insulin in simulated hostile biological environments

| Environment type & Exposure time span (hours) | Retention of particle-loaded insulin (%) | |
| --- | --- | --- |
| | Coated insulin fibrils | Insulin-gagomers |
| Simulated Intestinal Fluid, 2 hours | 47(±7)* | 95(±3) |
| Simulated Gastric Fluid, 2 hours | 81(±9) | 87(±4) |
| Simulated proteolytic environment (3 mg/ml Pronase), 0.5 hours | | 73(±9) |

In Vitro Evaluation of Insulin Activity in the Gagomeric Formulations

Figure 7:
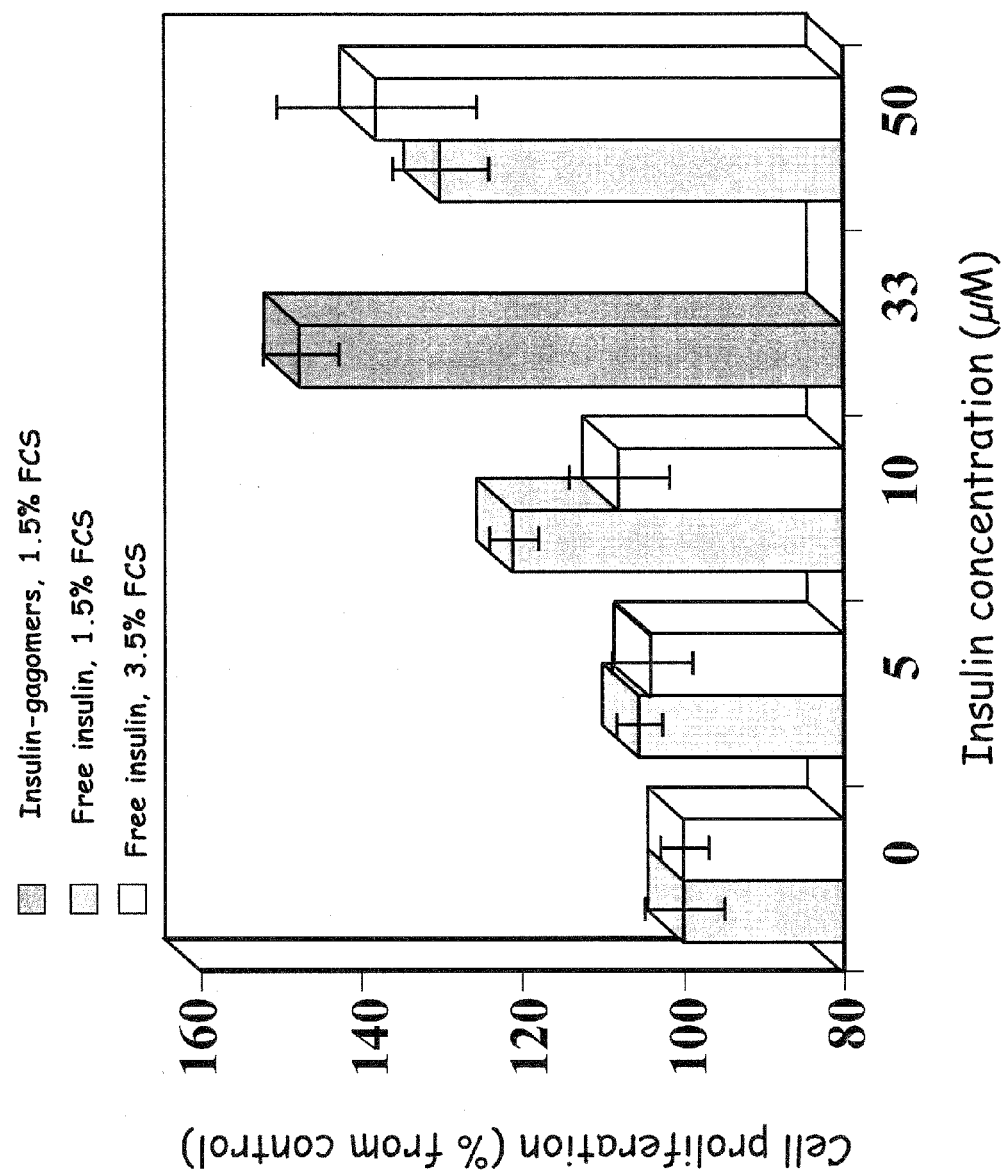
FIG. 7 is a graph of an in-vitro bioassay of free and of gagomeric insulin, in monolayers of NSCLC NCI-H2009 cells. Light gray bars: free insulin in media containing 1.5% FCS. White bars: same as the light gray bars except 3.5% FCS. Dark gray bar: insulin-gagomers in media containing 1.5% FCS. Each bar is an average of 6-8 wells, and the error bars represent the standard deviations.

As already discussed above, insulin monomers released upon dissociation of insulin fibrils are biologically active (Brange et al., 1997). To get some measure of whether the insulin loaded within the gagomers is active, before attempting in vivo studies, the ability of insulin to perform (under low-serum conditions) essentially as a growth factor stimulating cell proliferation was utilized. To that end, use was made of the cell line NCI-H2009, originating human non-small cell lung carcinoma. When the FCS level in the culture medium was reduced to 3.5% and to 1.5%, free insulin tested over the dose range of 0-50 µM, stimulated cell proliferation (FIG. 7). Testing under the same conditions insulin-gagomers that had an encapsulated insulin dose of 33 µM, it is clear that the gagomeric insulin is active at least on a par with free insulin.

In-Vivo Studies in Diabetic Mice

The diabetes onset, and the experimental protocols applied, detailed under the methods section, were the result of rigorous studies the present inventors previously performed with respect to modifications and refinements of this well-known model of streptozotocin (STZ)-induced diabetes in ICR mice (Dekel and Margalit 2007, in preparation).

It is imperative, when testing a novel insulin formulation in diabetic animals, to establish experimental conditions under which, during the time course of the experiment, there will be no significant drops in blood glucose levels (BGL) of the untreated animals. This is not always the case, as reported by others (Damge et al., 2007) and as also shown here in this study.

Figure 8:
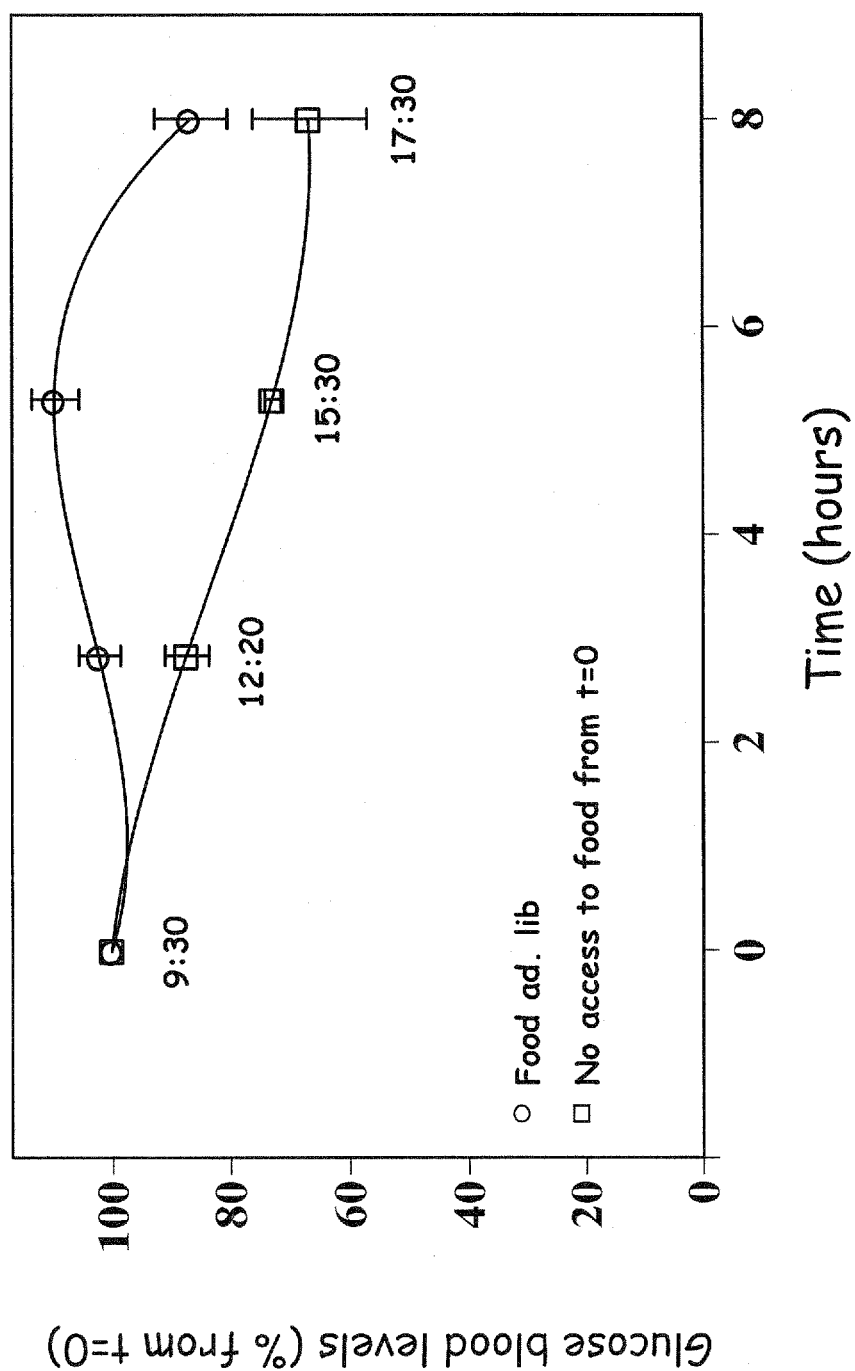
FIG. 8 is a graph of blood glucose levels (BGL) of untreated diabetic mice over a period of 8 hours, with (open circles) and without (open squares) access to food. The actual times of day at which blood was withdrawn for the glucose assay are listed in the figure. The points are the experimental data, each point an average of 8 mice, and the error bars are the SEM. The solid curves are non-theoretical, drawn to emphasize trends in the data.
Figures 12A, 12B, 12C, 12D:
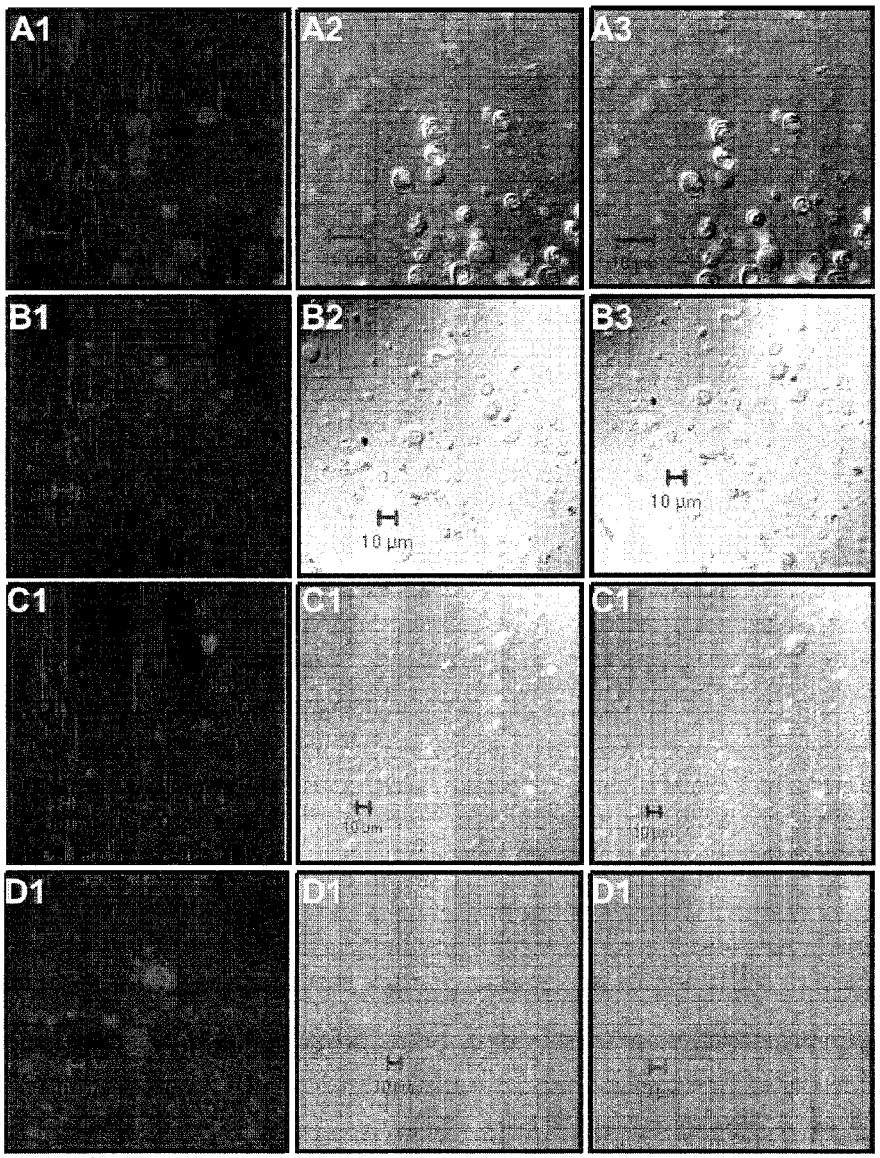
FIGS. 12A-12D show confocal microscopy images of labeled bioadhesive liposomes after 2 (FIG. 12A), 24 (FIG. 12B), 48 (FIG. 12C) and 96 (FIG. 12D) hours of incubation. Magnification ×40. Excitation and emission were at 543 nm and at 560 nm for DPPE-Rhodamine. The scale bar (bottom left) is 10 µm. Panels 1—the DPPE-Rhodamine image; 2—A composite of 1-3; 3—a Namarsky image.

Applying a frequently-used protocol of denying the animals food for the entire duration of the experiment, BGL of untreated animals drop significantly and in a progressive manner over the time span of 8 hours (FIG. 8). Such a drop can interfere with evaluating the full impact of a novel treatment. Allowing the animals continuous access to food, removed this difficulty. These untreated animals retained their initial BGL over most of the time span (FIG. 8). The minor drop after 6 hours can be attributed to normal glucose circadian fluctuation in mice. Based on these and additional studies, the present inventors settled on the following protocol for assessment of the novel insulin formulations: upon initiation of the experiment, food was taken away, and midway through the study, at the time point of 4 hours, the animals had access to food for 20 minutes. We wish to point out that such a protocol mimics human eating habits better than food denial for 8 hours or more. That this regimen was adequate for the untreated animals can be seen from the data in FIG. 9A.

At the outset, it should be re-emphasize what has already established in the field: It is not possible to match doses of insulin given by the conventional s.c. injection to those administered by routes other than systemic. The latter require significantly higher doses, whereas giving higher doses by s.c injection can be lethal (Cui et al., 2006; Morishita et al., 2006; Karmaker et al., 2006; Caleti et al., 2004).

As expected, free (non-fibrillar) insulin given orally was not effective, the animals response being similar to that of the no-treatment group (FIG. 9B vs. FIG. 9A). Another important control was performed with animals given the conventional insulin treatment of a s.c. injection. This served dual goals: to verify that the insulin was active and that the animals gave a proper response, and as a basis for comparing conventional response to the novel treatments. As shown in FIG. 9C, the animals responded well to the conventional treatment, especially at the early time points. Over the first hour post-injection blood glucose levels dropped to 30% of initial, and started rising thereafter.

The three types of fibrillar insulin fared significantly better than free (non-fibrillar) oral insulin. All three continuously decreased BGL over the entire 8 hour period (FIGS. 9D-9F). Plain fibrillar insulin, viewed as another control, was the least effective, bringing BGL down to roughly 60% of initial only at the latest time point (FIG. 9D). Both the coated insulin fibrils (FIG. 9E) and the gagomeric insulin (FIG. 9F) generated a continuous steady reduction of BGL, over the entire time range tested. For most of the range, the gagomeric insulin seems the better of the two, except at the last time point. Midway within the time span, the novel formulations perform on par or somewhat better than the conventional treatment. However, the continuous steady BGL decline generated by the novel formulations implies a potential for lowered risks of hypoglycemic events.

Recalling that the initial BGL (at time=0) was in the range of 400-600 mg/dl, the conventional treatment reduced the BGL down to levels of 120-180 mg/dl at its best—30 minutes post injection. The coated insulin fibrils and the gagomeric insulin brought the BGL levels at their best, 8 hours post-administration, to levels of 120-180 mg/dl, and 200-300 mg/dl, respectively. These are, for the most, normal BGL values for healthy mice under non-fasting conditions (Hayashi et al., 2006; and Cheng et al., 2006).

Monitoring the animal welfare throughout the experiments, from initiation of the diabetic state, through the treatments and beyond, the novel systems of the present invention indicated good safety. There was no significant weight loss, no animal death, no other overt signs of toxicity, and the animals exhibited normal behavior.

CONCLUSIONS

The experimental data reported here introduced two novel formulations of fibrillar insulin, designated for diabetes treatment, via oral administration.

Although distinct from each other, both systems utilize insulin fibrils as the stable insulin form loaded within the particles. Both formulations were found to be stable in environments simulating those they would encounter along the GIT, upon oral administration.

The impact of the novel insulin formulations on BGL glucose levels was tested in diabetic mice, under conditions that would best mimic the situation of diabetic patients. The in vivo results obtained in this study clearly show that both the coated insulin fibrils and the gagomeric insulin have high potential as orally-administered formulations for reduction and control of BGL.

It is too early to tell whether, from the aspect of BGL reduction, one of these formulations is better than the other. Clearly additional in vivo studies are required. It may turn out that both formulations provide similar-level BGL reductions, and that other requirements of pharmaceutical products will become the deciding factor.

The diabetics population is expected to benefit most from these novel formulations are type 2 diabetics, especially at the stage where insulin is needed to augment or replace their anti-diabetic drugs (such as metformin, sulfonylureas, and the newer drug classes). Formulations, such as those in the present invention that the patient can take orally at long enough intervals between dosings, may allow better BGL control and be significantly more patient-friendly than the current sc injection and future developments of other routes of administration.

Example 2

The study in this example is directed to coated insulin fibrils. Taking into consideration that insulin fibrils grow with time (Whittingham et al., 2002), acidic insulin was incubated with lyophilized powders of drug-free salt-free HA-BAL and fibril formation was followed over a time span of 2-192 hours. The "raw materials", namely the bioadhesive liposomes and separately, insulin, were also studied as controls.

Methods

The method and process for the formation of coated insulin fibrils is described in Example 1 in the Results and Discussion section entitled: "1b. Coated insulin fibrils". The method for following the formation of these particles with time, as well as for the fate of the two raw materials (insulin and bioadhesive liposomes) under the same conditions is as follows: The pH of the samples containing trace FITC-insulin and/or DPPE-Rhodamine (red fluorescent tag), was raised to 8, and 100 μl aliquots were pipetted onto a microscope slide glass and covered with a cover glass. The slides were viewed under a confocal microscope (ZEISS LSM 510, Carl Zeiss MicroImaging Gmbh, Gottingen, Germany). Excitation and emission were at 480 nm and 530 nm, respectively.

Results

1. Coated Insulin Fibrils

Confocal microscopy images (FIGS. 10A-10D) shed light on this process. As described under the methods section, double labeling was used for these experiments—DPPE-Rhodamine (red fluorescent tag) in the liposomal membrane and FITC-insulin (green fluorescent tag) for the insulin. Two hours into the incubation (FIG. 10A, panels 1-4), it is still possible to see intact liposome bundles. Most are weakly stained with FITC-insulin, but few seem to undergo self-interaction and to attract some insulin (still monomeric). Twenty-four hours later, changes are quite modest, reflecting further interaction between the insulin and the liposomes (FIG. 10B). At 48 hours (FIG. 10C) the liposomes disappear from the field and small rod like particles appear. At 96 hours (FIG. 10D) the newly-formed lipid-coated fibril particles appear. Lipid and insulin tightly coincide in the fibrillar particles (see FIG. 10, panels D1, D2 and especially D4), yet lipid material and fibrillar material can still be seen, separately, around the lipid-coated fibrils particles.

2. Control of Insulin Fibrils Alone

As shown in FIGS. 11A-11D, when insulin alone is subjected to the process described under methods it undergoes the expected fibrillation process.

3. Control of Bioadhesive Liposomes Alone

As shown in FIGS. 12A-12D, when the bioadhesive liposomes alone (i.e., no insulin in the system) are subjected to the process described under the methods section, they remain as intact liposomes undergoing no structural changes.

CONCLUSIONS

The processes discussed above and illustrated in FIGS. 10A-10D, are unique to the interactions of insulin and liposomes together, under the fibrillation conditions. Under similar conditions, neither insulin alone nor liposomes alone undergo such processes.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by references.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

Aigelsreiter, A., et al., *How a cell deals with abnormal proteins. Pathogenetic mechanisms in protein aggregation diseases.* Pathobiology, 2007. 74(3): p. 145-58.

Brange, J. and L. Langkjaer, *Chemical stability of insulin. 3. Influence of excipients, formulation, and pH.* Acta Pharm Nord, 1992. 4(3): p. 149-58.

Brange, J., et al., *Toward understanding insulin fibrillation.* J Pharm Sci, 1997. 86(5):517-25.

Brange, J., L. Andersen, E. D. Laursen, G. Meyn and E. Rasmussen, Toward understanding insulin fibrillation. *J Pharm Sci* 1997; 86; 5:517-25.

Calceti, P., et al., Development and in vivo evaluation of an oral insulin-PEG delivery system. *Eur J Pharm Sci,* 2004. 22(4): p. 315-23.

Carson F L: Histotechnology: a self instructional text; 7:136-136, 1990.

Cefalu, W. T., Concept, strategies, and feasibility of noninvasive insulin delivery. *Diabetes Care* 2004; 27:1:239-46.

Cheng, J., et al., Magnetically responsive polymeric microparticles for oral delivery of protein drugs. *Pharm Res,* 2006. 23(3): p. 557-6

Chi, E. Y., et al., *Physical stability of proteins in aqueous solution: mechanism and driving forces in nonnative protein aggregation.* Pharm Res, 2003. 20(9):1325-36.

Cui, F., et al., Biodegradable nanoparticles loaded with insulin-phospholipid complex for oral delivery: preparation, in vitro characterization and in vivo evaluation. *J Control Release,* 2006. 114(2):242-50.

Damge, C., P. Maincent, and N. Ubrich, Oral delivery of insulin associated to polymeric nanoparticles in diabetic rats. *J Control Release,* 2007. 117(2): p. 163-70.

Defelippis, M. R. and F. S. Larimore, *The role of formulation in insulin comparability assessments.* Biologicals, 2006. 34(1): p. 49-54.

Eisenberg, D., et al., *The structural biology of protein aggregation diseases: Fundamental questions and some answers.* Acc Chem Res, 2006. 39(9): p. 568-75.

Gazit, E., *The "Correctly Folded" state of proteins: is it a metastable state?* Angew Chem Int Ed Engl, 2002. 41(2): p. 257-9.

Gonzalez, C., D. Kanevsky, R. De Marco, G. Di Girolamo and S. Santoro, Non-invasive routes for insulin administration: current state and perspectives. *Expert Opin Drug Deliv* 2006; 3; 6:763-70.

Hayashi, K., R. Kojima, and M. Ito, Strain differences in the diabetogenic activity of streptozotocin in mice. *Biol Pharm Bull,* 2006. 29(6): p. 1110-9

Karmaker, S., et al., A novel drug delivery system for type 1 diabetes: insulin-mimetic vanadyl-poly(gamma-glutamic acid) complex. *J Inorg Biochem,* 2006. 100(9): p. 1535-46.

Klibanov, A. M. and J. A. Schefiliti, *On the relationship between conformation and stability in solid pharmaceutical protein formulations.* Biotechnol Lett, 2004. 26(14): p. 1103-6.

Lassmann-Vague, V. and D. Raccah, Alternatives routes of insulin delivery. *Diabetes Metab* 2006; 32; 5 Pt 2:513-22.

Margalit R., Liposome-mediated drug targeting in topical and regional therapies. *Crit Rev Ther Drug Carrier Syst* 12; 2-3, (1995) 233-61.

Margalit R., R. Alon, M1. Linenberg, I. Rubin, T. J. Roseman, R. W. Wood. Liposomal drug delivery: thermodynamic and chemical kinetic considerations. *J. Controlled Release* 17:285-296 (1991)

Morishita, M. and N. A. Peppas, Is the oral route possible for peptide and protein drug delivery? Drug Discov Today 2006; 11; 19-20:905-10.

Morishita, M., et al., Novel oral insulin delivery systems based on complexation polymer hydrogels: Single and multiple administration studies in type 1 and 2 diabetic rats. *J Control Release,* 2006. 110(3): p. 587-94.

Dan Peer and Rimona Margalit. Lipidated glycosaminoglycan particles and their use in drug and gene delivery for diagnosis and therapy. Published patent application US2004/0241248, US publication date 2004.

Peer, D. and R. Margalit, Physicochemical evaluation of a stability-driven approach to drug entrapment in regular and in surface-modified liposomes. *Arch Biochem Biophys* 2000; 383; 2:185-90.

Peer, D., A. Florentin and R. Margalit, Hyaluronan is a key component in cryoprotection and formulation of targeted unilamellar liposomes. *Biochim Biophys Acta* 2003; 1612; 1:76-82.

Richards, J. P., et al., *Self-association properties of monomeric insulin analogs under formulation conditions.* Pharm Res, 1998. 15(9): p. 1434-41.

Salman S. Rogers, Mark R. H. Krebs, Elizabeth H. C. Bromley, Erik van der Linden, and Athene M. Donald Optical Microscopy of Growing Insulin Amyloid Spherulites on Surfaces In Vitro. *Biophysical Journal* 2006, 90; 1043-1054.

Sandri, G., S. Rossi, F. Ferrari, M. C. Bonferoni, N. Zerrouk and C. Caramella, Mucoadhesive and penetration enhancement properties of three grades of hyaluronic acid using porcine buccal and vaginal tissue, Caco-2 cell lines, and rat jejunum. *J Pharm Pharmacol* 2004; 56; 9:1083-90.

Schellekens, H., *When biotech proteins go off-patent.* Trends Biotechnol, 2004. 22(8): p. 406-10.

Sharon Fischer, Aya Arad and Rimona Margalit. Lipsome-formulated enzymes for organophosphate scavenging: Butyrylcholinesterase and Demeton-S. *Arch. Biochem. Biophys.* 434 (2005) 108-115

US Pharmacopeia 27 NF 22, The United States Pharmacopoeia, page 2724, (2004)

Whittingham, J. L., et al., Insulin at pH 2: structural analysis of the conditions promoting insulin fibre formation. *J Mol Biol* 2002; 318; 2:479-90.

Yerushalmi, N. and R. Margalit, Hyaluronic acid-modified bioadhesive liposomes as local drug depots: effects of cellular and fluid dynamics on liposome retention at target sites. *Arch Biochem Biophys* 349; 1, (1998) 21-6.

Yerushalmi, N. and R. Margalit, Bioadhesive, collagen-modified liposomes: molecular and cellular level studies on the kinetics of drug release and on binding to cell monolayers. *Biochim Biophys Acta* 1189; 1, (1994) 13-20.

Yerushalmi, N., A. Arad and R. Margalit, Molecular and cellular studies of hyaluronic acid-modified liposomes as bioadhesive carriers for topical drug delivery in wound healing. *Arch Biochem Biophys* 313; 2, (1994) 267-73.

What is claimed is:

1. A pharmaceutical composition, comprising a pharmaceutically acceptable carrier, diluent, excipient or auxiliary agent and, as active ingredient, either fibrils or insoluble aggregates of insulin, which fibrils or insoluble aggregates are capable of dissociating and releasing soluble monomers of insulin in therapeutically active form, where said fibrils or insoluble aggregates are (a) encapsulated in a lipidated glycosaminoglycan particle, which comprises the reaction product of at least one glycosaminoglycan with at least one lipid having a primary amino group, (b) coated with a multi-layer of at least two lipids and conjugates of one of said at least two lipids and at least one glycosaminoglycan, or (c) present as unencapsulated and uncoated fibrils or insoluble aggregates.

2. The pharmaceutical composition of claim 1, wherein said fibrils or insoluble aggregates of insulin are encapsulated in said lapidated glycosaminoglycan particle.

3. The pharmaceutical composition of claim 2, wherein one of said lipid(s) is a phosphatidylethanolamine.

4. The pharmaceutical composition of claim 3, wherein said phosphatidylethanolamine is dipalmitoyl phosphatidylethanolamine.

5. The pharmaceutical composition of claim 1, which is adapted for oral administration.

6. The pharmaceutical composition of claim 2, wherein said at least one glycosaminoglycan is hyaluronic acid.

7. The pharmaceutical composition of claim 2, wherein the size of said lipidated glycosaminoglycan particle is in a range of about 10 to 100 microns.

8. The pharmaceutical composition of claim 2, which is adapted for oral administration.

9. A method for treating diabetes, comprising orally administering to a subject in need thereof an effective amount of the pharmaceutical composition of claim 8.

10. A method for preparing the active ingredient of the pharmaceutical composition of claim 2, comprising:
    reacting at least one glycosaminoglycan with at least one lipid containing a primary amino group to cross-link the carboxylic residue of the glycosaminoglycan with the primary amino group to produce lipidated glycosaminoglycan particles (gagomers);
    removing excess glycosaminoglycan, excess lipids and reaction by-products from the produced gagomers;
    suspending said gagomers in a salt-free buffer which is capable of being vaporized upon lyophilization;
    lyophilizing said gagomers to vaporize the buffer, resulting in a salt-free, buffer-free lyophilized powder of said gagomers; and
    rehydrating said salt-free, buffer-free lyophilized powder of said gagomers with an aqueous solution of insulin under conditions suitable for fibrillation or aggregation to encapsulate said therapeutic protein insulin as insoluble fibrils or aggregates in said gagomers.

11. The method of claim 10, wherein said at least one glycosaminoglycan is hyaluronan.

12. The method of claim 10, wherein said at least one of said lipid(s) is a phosphatidylethanolamine.

13. The method of claim 12, wherein said phosphatidylethanolamine is dipalmitoylphosphatidlyethamolamine.

14. The method of claim 10, wherein said salt-free buffer for suspending said gagomers is an ammonium bicarbonate buffer and the insulin is insulin acidified to a pH of about 2 suitable for forming fibrils.

15. The pharmaceutical composition of claim 1, wherein said fibrils or insoluble aggregates of insulin are coated with said multi-layer of at least two lipids and conjugates of one of said at least two lipids said at least one glycosaminoglycan.

16. The pharmaceutical composition of claim 15, which is adapted for oral administration.

17. A method for treating diabetes, comprising orally administering to a subject in need thereof an effective amount of the pharmaceutical composition of claim 16.

18. A method for preparing the active ingredient of the pharmaceutical composition of claim 15, comprising:
    reacting at least one glycosaminoglycan with liposomes comprising at least two lipids to produce multi-lamellar liposomes having said at least one glycosaminoglycan covalently anchored as a bioadhesive ligand;
    removing excess glycosaminoglycan, excess lipids and reaction by-products from the produced multi-lamellar liposomes;
    suspending the multi-lamellar liposomes in a salt-free buffer which is capable of being vaporized upon lyophilization;
    lyophilizing the multi-lamellar liposomes to vaporize the buffer, resulting in a salt-free, buffer-free lyophilized powder of the multi-lamellar liposomes; and rehydrating said salt-free, buffer-free lyophilized powder of the multi-lamellar liposomes with an aqueous solution of insulin under conditions suitable for fibrillation or aggregation to coat the insoluble fibrils or aggregates formed under said conditions with a multi-layer of at least two lipids and conjugates of one of said at least two lipids and said at least one glycosaminoglycan.

19. The method of claim 18, wherein said at least one glycosaminoglycan is hyaluronan.

20. The method of claim 18, wherein one of said at least two lipids is a phosphatidylethanolamine.

21. The method of claim 18, wherein the liposomes and said at least one glycosaminoglycan are covalently linked by glutaraldehyde.

22. The method of claim 18, wherein the liposomes and said at least one glycosaminoglycan are cross-linked with 1-ethyl-3(3-dimethylaminoprophyl) carbodiimide.

23. The method of claim 18, wherein said salt-free buffer for suspending said multi-lamellar liposomes is an ammonium bicarbonate buffer and the insulin is insulin acidified to a pH of about 2 suitable for forming fibrils.

24. The pharmaceutical composition of claim 1, wherein said fibrils or insoluble aggregates of insulin are present as unencapsulated and uncoated fibrils or insoluble aggregates.

25. The pharmaceutical composition of claim 24, which is adapted for oral administration.

26. A method for treating diabetes, comprising orally administering to a subject need thereof an effective amount of the pharmaceutical composition of claim 25.

27. A scaffold for tissue engineering, comprising insoluble fibrils or aggregates of insulin encapsulated in a lapidated glycosaminoglycan particle, which comprises the reaction product of at least one glycosaminoglycan with a least one lipid having a primary amino group, or coated with a multi-layer of at least two lipids and conjugates of one of said at least two lipids and at least one glycosaminoglycan.

28. The pharmaceutical composition of claim 15, wherein said at least one glycosaminoglycan is hyaluronic acid.

29. The pharmaceutical composition of claim 15, wherein one of said lipid(s) is a phosphatidylethanolamine.

30. The pharmaceutical composition of claim 29, wherein said phosphatidylethanolamine is dipalmitoyl phosphatidylethanolamine.

31. The pharmaceutical composition of claim 24, wherein said at least one glycosaminoglycan is hyaluronic acid.

32. The pharmaceutical composition of claim 24, wherein one of said lipid(s) is a phosphatidylethanolamine.

33. The pharmaceutical composition of claim 32, wherein said phosphatidylethanolamine is dipalmitoyl phosphatidylethanolamine.

* * * * *